(12) United States Patent
Monte et al.

(10) Patent No.: US 11,559,486 B2
(45) Date of Patent: Jan. 24, 2023

(54) READY-TO-USE FORMULATION FOR VINCRISTINE SULFATE LIPOSOME INJECTION

(71) Applicant: Spectrum Pharmaceuticals, Inc., Henderson, NV (US)

(72) Inventors: William T. Monte, Lincolnshire, IL (US); Robert Malcolm Abra, San Francisco, CA (US); Bing Luo, Fremont, CA (US); Yuanpeng Zhang, Cupertino, CA (US)

(73) Assignee: Acrotech Biopharma, LLC, East Windsor, NJ (US)

( * ) Notice: Subject to any disclaimer, the term of this patent is extended or adjusted under 35 U.S.C. 154(b) by 0 days.

(21) Appl. No.: 15/735,488

(22) PCT Filed: Jul. 22, 2016

(86) PCT No.: PCT/US2016/043622
§ 371 (c)(1),
(2) Date: Dec. 11, 2017

(87) PCT Pub. No.: WO2017/015584
PCT Pub. Date: Jan. 26, 2017

(65) Prior Publication Data
US 2018/0153805 A1 Jun. 7, 2018

Related U.S. Application Data

(60) Provisional application No. 62/195,711, filed on Jul. 22, 2015.

(51) Int. Cl.
*A61K 9/127* (2006.01)
*A61K 31/475* (2006.01)
(Continued)

(52) U.S. Cl.
CPC ............ *A61K 9/127* (2013.01); *A61K 9/0019* (2013.01); *A61K 31/475* (2013.01); *A61K 45/06* (2013.01); *A61P 35/02* (2018.01)

(58) Field of Classification Search
CPC ...... A61K 9/127; A61K 9/0019; A61K 45/06; A61K 31/475; A61K 47/20; A61K 9/107; A61P 35/02; A61P 35/00
See application file for complete search history.

(56) References Cited

U.S. PATENT DOCUMENTS

| 2,932,718 A | 4/1960 | Marsters |
| 4,186,183 A | 1/1980 | Steck et al. |

(Continued)

FOREIGN PATENT DOCUMENTS

| JP | S59-29617 | 2/1984 |
| JP | H2-196713 | 8/1990 |

(Continued)

OTHER PUBLICATIONS

Trosko, J.E., Mutation Researvh 480-481, pp. 219-229, 2001.*
(Continued)

*Primary Examiner* — Gollamudi S Kishore
(74) *Attorney, Agent, or Firm* — K&L Gates LLP; Louis C. Cullman; Hal Gibson

(57) ABSTRACT

Disclosed herein are various compositions comprising neoplastic formulations and their methods of use.

40 Claims, 1 Drawing Sheet

(51) Int. Cl.
  *A61K 45/06* (2006.01)
  *A61K 9/00* (2006.01)
  *A61P 35/02* (2006.01)

(56) References Cited

U.S. PATENT DOCUMENTS

| | | |
|---|---|---|
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,603,044 A | 7/1986 | Geho et al. |
| 4,737,323 A | 4/1988 | Martin et al. |
| 4,774,085 A | 9/1988 | Fidler |
| 4,837,028 A | 6/1989 | Allen |
| 4,885,172 A | 12/1989 | Bally et al. |
| 4,906,476 A | 3/1990 | Radhakrishnan |
| 4,920,016 A | 4/1990 | Allen et al. |
| 4,946,787 A | 8/1990 | Eppstein et al. |
| 4,952,408 A | 8/1990 | Rahman |
| 4,957,773 A | 9/1990 | Spencer et al. |
| 4,971,802 A | 11/1990 | Tarcsay et al. |
| 5,023,087 A | 6/1991 | Yau-Young |
| 5,059,421 A | 10/1991 | Loughrey et al. |
| 5,077,056 A | 12/1991 | Bally et al. |
| 5,165,922 A | 11/1992 | Hellstrom et al. |
| 5,171,578 A | 12/1992 | Bally et al. |
| 5,192,549 A | 3/1993 | Barenolz et al. |
| 5,262,168 A | 11/1993 | Lenk et al. |
| 5,397,784 A | 3/1995 | Gazdag et al. |
| 5,417,978 A | 5/1995 | Tari et al. |
| 5,534,499 A | 7/1996 | Ansell |
| 5,543,152 A | 8/1996 | Webb et al. |
| 5,552,154 A | 9/1996 | Giovanella et al. |
| 5,552,156 A | 9/1996 | Burke |
| 5,567,592 A | 10/1996 | Benet et al. |
| 5,595,756 A * | 1/1997 | Bally ............... A61K 9/1272 264/4.1 |
| 5,648,090 A | 7/1997 | Rahman |
| 5,714,163 A | 2/1998 | Forssen et al. |
| 5,736,155 A | 4/1998 | Bally et al. |
| 5,741,516 A * | 4/1998 | Webb ............... A61K 9/1272 424/450 |
| 5,755,788 A | 5/1998 | Strauss |
| 5,762,957 A | 6/1998 | Mehlhorn |
| 5,785,987 A | 7/1998 | Hope et al. |
| 5,814,335 A | 9/1998 | Webb et al. |
| 5,820,873 A | 10/1998 | Choi et al. |
| 5,837,282 A | 11/1998 | Fenske et al. |
| 5,885,613 A | 3/1999 | Holland et al. |
| 5,888,537 A | 3/1999 | Forssen et al. |
| 5,976,567 A | 11/1999 | Wheeler et al. |
| 6,056,973 A | 5/2000 | Allen et al. |
| 6,090,407 A | 7/2000 | Knight et al. |
| 6,110,491 A | 8/2000 | Kirprotin |
| 6,129,914 A | 10/2000 | Weiner et al. |
| 6,316,024 B1 | 11/2001 | Allen et al. |
| 6,320,017 B1 | 11/2001 | Ansell |
| 6,352,996 B1 | 3/2002 | Cao et al. |
| 6,355,268 B1 | 3/2002 | Slater et al. |
| 6,471,943 B1 | 10/2002 | Placke et al. |
| 6,548,071 B1 | 4/2003 | Chervian |
| 6,566,395 B1 | 5/2003 | Moran |
| 6,627,614 B1 | 9/2003 | Rubinfeld |
| 6,653,319 B1 | 11/2003 | Xiang et al. |
| 6,664,233 B1 | 12/2003 | Rubinfeld |
| 6,723,338 B1 | 4/2004 | Sarris et al. |
| 6,740,335 B1 | 5/2004 | Moynihan et al. |
| 6,825,206 B1 | 11/2004 | Gamcsik et al. |
| 6,855,331 B2 | 2/2005 | Vook et al. |
| 7,060,828 B2 | 6/2006 | Madden et al. |
| 7,094,423 B1 | 8/2006 | Maurer et al. |
| 7,244,448 B2 | 7/2007 | Madden et al. |
| 7,244,450 B2 | 7/2007 | Sarris et al. |
| 7,247,316 B2 | 7/2007 | Sarris et al. |
| 7,311,924 B2 | 12/2007 | Sarris et al. |
| 7,452,550 B2 | 11/2008 | Madden et al. |
| 7,811,602 B2 | 10/2010 | Cullis et al. |
| 7,887,836 B2 | 2/2011 | Sarris et al. |
| 8,147,867 B2 | 4/2012 | Hong et al. |
| 8,329,213 B2 | 12/2012 | Hong et al. |
| 8,871,253 B2 | 10/2014 | Li et al. |
| 2001/0016196 A1 | 8/2001 | Benz et al. |
| 2003/0091621 A1 | 5/2003 | Tardi et al. |
| 2003/0147945 A1 | 8/2003 | Tardi et al. |
| 2003/0219476 A1 | 11/2003 | Ahmad et al. |
| 2004/0071768 A1 | 4/2004 | Sarris et al. |
| 2004/0170678 A1 | 9/2004 | Madden et al. |
| 2004/0171768 A1 | 9/2004 | Miho |
| 2005/0118250 A1 | 6/2005 | Tardi et al. |
| 2005/0129750 A1 | 6/2005 | Hu et al. |
| 2006/0008535 A1 | 1/2006 | Sabin |
| 2006/0008909 A1 | 1/2006 | Cullis et al. |
| 2006/0093662 A1 | 5/2006 | Madden et al. |
| 2006/0222694 A1 | 10/2006 | Oh et al. |
| 2006/0257465 A1 | 11/2006 | Maurer et al. |
| 2006/0269594 A1 | 11/2006 | Madden et al. |
| 2007/0292322 A1 | 12/2007 | Soung et al. |
| 2009/0028933 A1 | 1/2009 | Thomas |
| 2009/0285878 A1 | 11/2009 | Hope et al. |
| 2010/0119590 A1 * | 5/2010 | Hu ..................... A61P 31/00 514/214.02 |
| 2011/0086826 A1 | 4/2011 | Madden et al. |
| 2012/0003297 A1 | 1/2012 | Sarris et al. |
| 2012/0164211 A1 | 6/2012 | Thomas |
| 2012/0201874 A1 | 8/2012 | Li et al. |
| 2013/0052259 A1 * | 2/2013 | Barenholz .......... A61K 9/1271 424/450 |
| 2013/0136787 A1 | 5/2013 | Madden et al. |
| 2013/0236534 A1 * | 9/2013 | Cullis ................ A61K 9/127 424/450 |
| 2014/0170075 A1 * | 6/2014 | Drummond .......... A61P 35/00 424/9.32 |
| 2015/0030672 A1 * | 1/2015 | Li ..................... A61K 9/1271 264/4.7 |
| 2015/0290184 A1 | 10/2015 | Monte et al. |

FOREIGN PATENT DOCUMENTS

| | | |
|---|---|---|
| JP | 9-504517 | 5/1997 |
| JP | 2003-510239 A | 3/2003 |
| JP | 2004-501955 A | 1/2004 |
| JP | 2004-277374 | 10/2004 |
| JP | 2009-219497 | 10/2009 |
| JP | 2013-063923 | 4/2013 |
| WO | 1988/004924 A1 | 7/1988 |
| WO | 1988/006442 A1 | 9/1988 |
| WO | 1989/011292 A1 | 11/1989 |
| WO | 1990/014105 A1 | 11/1990 |
| WO | 1991/004019 A1 | 4/1991 |
| WO | 1991/017424 A1 | 11/1991 |
| WO | 1994/020145 A1 | 9/1994 |
| WO | 1995/008986 A1 | 4/1995 |
| WO | 1995/035094 A1 | 12/1995 |
| WO | 1996/000057 A1 | 1/1996 |
| WO | 1998/017256 A1 | 4/1998 |
| WO | 1999/013816 A2 | 3/1999 |
| WO | 1999/051202 A2 | 10/1999 |
| WO | 2000/023052 A1 | 4/2000 |
| WO | 00/59473 * | 10/2000 |
| WO | 2000/059473 A1 | 10/2000 |
| WO | 2002/002077 A2 | 1/2002 |
| WO | 2002/002078 A2 | 1/2002 |
| WO | 2004/017940 A2 | 3/2004 |
| WO | 2005/002546 A1 | 1/2005 |
| WO | 2005/107712 A1 | 11/2005 |
| WO | 2006/052767 A1 | 5/2006 |
| WO | 2009/108530 A2 | 9/2009 |
| WO | 2010/100686 | 9/2010 |
| WO | 2011/125848 A1 | 10/2011 |
| WO | 2012/138938 A1 | 10/2012 |
| WO | 2013/123407 A1 | 8/2013 |

(56) References Cited

FOREIGN PATENT DOCUMENTS

| WO | 2014/081887 A1 | | 5/2014 |
|---|---|---|---|
| WO | 2014081887 | * | 5/2014 |
| WO | 2017/015584 A1 | | 1/2017 |

OTHER PUBLICATIONS

Shan, S., et al in Cancer Chemother Pharmacol vol. 58, pp. 245-255, 2006.*

Lundberg, Bo. B., Biologically active camptothecin derivatives for incorporation into liposome bilayers and lipid emulsions. Anti-Cancer Drug Design, vol. 13:453-461 (1998).

Luo et al., Studies on polyphase liposome of camptothecin, PL-CSA. Yao xue xue bao, Acta Pharmaceutica Sinica, vol. 19(1):63-68 (1984). (full Chinese article and English abstract.

Lynam et al., Camptothecin analogue efficacy in vitro: Effect of liposomal encapsulation of GI147211C (Lurtotecan) on in vitro cytotoxicity for multiple tumor cell types. Proceedings of the American Association for Cancer Research, vol. 39: 421, Poster No. 2863 (1998) (2 pages).

Lynam et al., Camptothecin analogue efficacy in vitro: Effect of liposomal encapsulation of GI147211C (NX211). Drug Delivery, vol. 6:51-62 (1999).

Mackenzie et al., A phase I study of OSI-211 and cisplatin as intravenous infusions given on days 1, 2 and 3 every 3 weeks in patients with solid cancers. Annals of Oncology, vol. 15:665-670 (2004).

Madden et al., Encapsulation of topotecan in lipid-based carrier systems. Evaluation of drug stability and plasma elimination in a murine model, and comparison of antitumor efficacy against murine L1210 and B16 Tumors. Proceedings of ASCO, vol. 17:196a, Abstract No. 754 (1998).

Madden et al., The accumulation of drugs within large unilamellar vesicles exhibiting a proton gradient: a survey. Chemistry and Physics of Lipids, vol. 53:37-46 (1990).

Maliepaard et al., Circumvention of breast cancer resistance protein (BCRP)-mediated resistance to camptothecins in vitro using non-substrate drugs or the BCRP inhibitor GF120918. Clinical Cancer Research, vol. 7:935-941 (2001).

Mamot et al., Liposome-based approaches to overcome anticancer drug resistance. Drug Resistance Updates, vol. 6:271-279 (2003).

Mayer et al., Solute distributions and trapping efficiencies observed in freeze-thawed multilamellar vesicles. Biochimica et Biophysica Acta, vol. 817:193-196 (1985).

Mayer et al., Characterization of liposomal systems containing doxorubicin entrapped in response to pH gradients. Biochimica et Biophysica Acta, vol. 1025:143-151 (1990).

Mayer et al., Liposomal vincristine preparations which exhibit decreased drug toxicity and increased activity against murine L1210 and P388 Tumors. Cancer Research, vol. 50:575-579 (1990).

Mayer et al., Identification of vesicle properties that enhance the antitumor activity of liposomal vincristine against murine L1210 leukemia. Cancer Chemother. Pharmacol., vol. 33:17-24 (1993).

Mayer et al., Vesicles of variable sizes produced by a rapid extrusion procedure. Biochim. Et Biophys. Acta 858:161-168 (1986).

Mayer et al., Techniques for encapsulating bioactive agents into liposomes. Chem. and Phys. of Lipids 40:333-345 (1986).

Mccabe et al., Comparative activity of oral and parenteral topotecan in murine tumor models: Efficacy of oral topotecan. Cancer Investigation, vol. 12(3):308-313 (1994).

Meerum et al., Clinical pharmacology of anticancer agents in relation to formulations and administration routes. Cancer Treatment Reviews, vol. 25:83-101 (1999).

Messerer et al., Liposomal irinotecan: Formulation development and therapeutic assessment in murine xenograft models of colorectal cancer. Clinical Cancer Research, vol. 10:6638-6649 (2004).

Michaelis et al., Cationic liposomes (catioms) to target tumor neovasculature. Abstracts of Papers, American Chemical Society, in Proceedings of the 226th ASC National Meeting, Abstract No. 2 (2003).

Mi et al., Differential interactions of camptothecin lactone and carboxylate forms with human blood components. Biochemistry, vol. 33:10325-10336 (1994).

Nyholm et al., Properties of palmitoyl phosphatidylcholine, sphingomyelin, and dihydrosphingomyelin bilayer membranes as reported by different fluorescent reporter molecules. Biophysical Journal, vol. 84:987-997 (2003).

O'Brien et al., A phase 2 study to evaluate the safety and efficacy of weekly doses of Marqibo® (liposomal vincristine sulfate) in adult patients with Philadelphia Chromosome-Negative Acute Lymphoblastic Leukemia (Ph ALL) in second relapse or who progressed following two treatment lines. 52nd ASH Annual Meeting and Exposition, New Orleans, LA (2009).

O'Brien et al., Pivotal phase 2 study of weekly vincristine sulfate liposomes injection (VSLI, Marquibo®) in adults with philadephia chromosome-negative actue lymphoblastic leukemia (ALL) in second relapse or progressing following two anit-leukemia treatment lines. Blood, vol. 114, Issue 22, Abstract 3088 (2009).

O'Leary et al., Antiangiogenic effects of camptothecin analogues 9-Amino-20(S)-camptothecin, topotecan, and CPT-11 studied in the mouse cornea model. Clinical Cancer Research, vol. 5:181-187 (1999).

Ormrod et al., Topotecan. A Review of its efficacy in small cell lung cancer. Drugs, vol. 58(3):533-551 (1999).

Paciucci et al., Mitoxantrone, vincristine, and dexamethasone in pateints with refractory lymphoma. Am. J. Clin. Oncol. (CCT) 12(4), pp. 327-331 (1989).

Pal et al., Enhanced antitumor efficacy of liposome-based formulation of SN38 against human pancreatic tumor in SCID mice. Proceedings of the American Association for Cancer Research, Abstract No. 1785 (2003).

Parovichnikova, et al., Superhigh doses of dexamethasone in treatment of refractory forms of acute lymphoblast of adults. Ter. Arkh., vol. 75(7):21-23 (2003). Abstract only.

Plowman et al., Human tumor xenograft models in NCI drug development. Anticancer Drug Development Guide: Preclinical Screening, Clinical Trials, and Approval, B. Teicher (Ed.), Humana Press Inc., Totowa, N.J., Chpt. 6, pp. 101-125 (1997).

Poirot et al., Liposomal-camptothecin composed of cationic phospholipids containing unsturated fatty acids: Formulation and cytotoxicity studies. Proceedings of the American Association for Cancer Research, vol. 37:300, Abstract 2039 (1996).

Proulx et al., Incorporation of campthothecin into liposomes: a new approach for the treatment of leishmaniasis. Abstracts of the 39th Annual Interscience Conference on Antimicrobial Agents and Chemotherapy, pp. 730-731, Abstract No. 1856 (1999).

Proulx et al., Treatment of visceral leishmaniasis with sterically stabilized liposomes containing camptothecin. Antimicrobial Agents and Chemotherapy, vol. 45(9):2623-2627 (2001).

Quasthoff et al., Chemotherapy-induced peripheral neuropathy. J. Neurol., vol. 249:9-17 (2002).

Renneisen et al., Inhibition of expression of human immunodeficiency vivrus-1 in vitro by antibody-targeted liposomes containing antisense RNA to the env region. J. Biol. Chem. 265(27):16337-16342 (1990).

Rodriguez et al., Phase II study of sphingosomal vincristine in CHOP+/- Rituximab for patients with aggressive Non-Hodgkin's Lymphoma (NHL):Promising 3 Year follow-up results in elderly patients. Blood, vol. 106(11):277a, Poster Session 943 (2005).

Rodriguez et al., Sphingosomal vincristine in CHOP is a promising new treatment for elderly, as well as poor prognosis patients with aggressive non-Hodgkin's lymphoma (NHL): Follow-up results of a phase II study. Journal of Clinical Oncology, Proceedings of the 2004 ASCO Annual Meeting, vol. 22(14S) Poster Session 8080 (2004).

Rodriguez, M.A. et al., Vincristine Sulfate Liposomes Injection (Marqibo) in heavily pretreated patients with refractory aggressive non-hodgkin lymphoma. Cancer, vol. 115:3475-3482 (2009).

Sadzuka et al., Antitumor effect of CPT-11 encapsulated liposome and conversion to active metabolite. J. Liposome Res., pp. 101-102 (1998).

Sadzuka, Y., Effective prodrug liposome and conversion to active metabolite. Current Drug Metabolism, vol. 1:31-48 (2000).

(56) References Cited

OTHER PUBLICATIONS

Sadzuka et al., Effect of liposomalization on the antitumor activity, side-effects and tissue distribution of CPT-11. Cancer Letters, vol. 127:99-106 (1998).
Sadzuka et al., Effective irinotecan (CPT-11)-containing liposomes: Intraliposomal conversion to the active metabolite SN-38. Jpn. J. Cancer Res., vol. 90:226-232 (1999).
Sadzuka et al., The study of polyethyleneglycol-coated liposomes containing CPT-11. Journal of Liposome Research, vol. 7(2&3):241-260 (1997).
Sarkar et al., Toxicity Evaluation of a liposome-based formulation of SN38 in mice. Toxicol. Sci., vol. 72 (S-1 ):83, Abstract No. 403 (2003).
Sarris et al., Liposomal vincristine in relapsed non-Hodgkin's lymphomas: Early results of an ongoing phase II trial. Annals of Oncology, vol. 11:69-72 (2000).
Saxon et al., Lipsomal anticancer drugs as agents to be used in combination with other anticancer agents: studies on a liposomal formulation with two encapsulated drugs. Journal of Liposome Research, 9(4), pp. 507-522 (1999) (Abstract only).
Schiffelers et al., In vivo synergistic interaction of liposome-coencapsulated gentamicin and ceftazidime. The Journal of Pharmacology and Experimental Therapeutics, 298(1), pp. 369-375, 2001.
Seiden et al., A phase II study of liposomal lurtotecan (OSI-211) in patients with topotecan resistant ovarian cancer. Gynecologic Oncology, vol. 93:229-232 (2004).
Semple et al., Comparative efficacy and therapeutic index of topotecan and liposomal topotecan in murine and human solid tumor models. Proceedings of the American Association for Cancer Research, vol. 44, Abstract No. 3658 (2003).
Semple et al., Pre-clinical evaluation of liposomal topotecan: increased efficacy and therapeutic index in murine and human xenograft tumor models compared to free drug. Proceedings of the American Association for Cancer Research. vol. 42:374, Abstract No. 2015 (2001).
Stano et al., Novel camptothecin analogue (Gimatecan)-containing liposomes prepared by the ethanol injection method. Journal of Liposome Research, vol. 14(1&2):87-109 (2004).
Grochow et al., Pharmacokinetics and pharmacodynamics of topotecan in patients with advanced cancer. Drug Metabolism and Disposition, vol. 20(5):706-713 (1992).
Gruner, Sol M., Materials properties of liposomal bilayers. Liposomes: From Biophysics to Therapeutics, Ostro, M.J. (Ed.), Marcel Dekker, New York, Chp. 1, pp. 1-38 (1987).
Guo et al., Determination by liquid chromatography with fluorescence detection of total 7-ethyl-10-hydroxy-camptothecin (SN-38) in beagle dog plasma after intravenous administration of liposome-based SN-38 (LE-SN38). Journal of Chromatography B, vol. 791:85-92 (2003).
Haas et al., Strong antitumor efficacy of a cationic liposomal camptothecin formulation (LipoCamTM) in the subcutaneous human melanoma. Proceedings of the American Association for Cancer Research, vol. 44(2nd ed.):350-351, Abstract No. R1793 (2003).
Haim et al., Full dose vincristine (without 2-mg Dose Limit) in the treatment of lymphomas. Cancer, vol. 73 (10):2515-2519 (1994).
Hardman et al., Efficacy of treatment of colon, lung and breast human carcinoma xenografls with: Doxorubicin, cisplatin, irinotecan or topotecan. Anticancer Research, vol. 19:2269-2274 (1999).
Hatefi et al., Review: Camptothecin delivery methods. Pharmaceutical Research, vol. 19(10):1389-1399 (2002).
Heath, T., Covalent attachment of proteins to lipsomes. Methods in Enzymology, 149:111-119 (1987).
Heath et al., Covalent attachment of immunoglobulins to liposomes via glycosphingolipids. Biochimica et Biophysica Acta, vol. 640:68-81 (1981).
Hope et al., Generation of multilamellar and unilamellar phospholipid vesicles. Chemistry and Physics of Lipids, vol. 40:89-107 (1986).
Hope et al., Production of large unilamellar vesicles by a rapid extrusion procedure. Characterization of size distribution, trapped volume and ability to maintain a membrane potential. Biochim. Et Biophys. Acta 812:55-65 (1985).
Hsiang et al., Identification of mammalian DNA topoisomerase I as an intracellular target or the anticancer drug camptothecin. Cancer Research, vol. 48:1722-1726 (1988).
Hudson et al., Xenotransplantation of human lymphoid malignancies is optimized in mice with multiple immunologic defects Leukemia, 12(12):2029-2033 (1998).
International Preliminary Report on Patentability for Application No. PCT/US2005/040061, dated Jun. 26, 2007.
International Search Report for Application No. PCT/CA01/00981 dated Aug. 29, 2002.
International Preliminary Examination Report Application No. PCT/CA01/00981 dated Nov. 22, 2002.
International Search Report for Application No. PCT/CA01/00925 dated Aug. 29, 2002.
International Preliminary Examination Report for Application No. PCT/CA01/00925 dated Nov. 22, 2002.
International Search Report for Application No. PCT/US2005/040061 dated May 30, 2007.
International Search Report for Application No. PCT/US00/08669 dated Jul. 9, 2000.
International Search Report for Application No. PCT/US2005/028233 dated Jan. 5, 2006.
Preliminary Report on Patentability for Application No. PCT/US2005/028233 dated Feb. 13, 2007.
Written opinion for Application No. PCT/US2005/028233 dated Jan. 2006.
Jackson et al., Intravenous vincristine infusion: phase I trial. Cancer, vol. 48:2559-2564 (1981).
Jackson et al., Treatment of advanced non-hodgkin's lymphoma with vincristine infusion. Cancer, vol. 53:2601-2606 (1984).
Kamath et al., Therapeutic efficacy of liposome-based formulation of SN38 against leukemia model in CD2F1 mice. Proceedings of the American Association for Cancer Research, vol. 44, 2nd Ed., Abstract No. 1784 (2003).
Kantarjian et al., Acute lymphocytic leukaemia in the elderly: characteristics and outcome with the vincristine-adriamycin-dexamethasone (VAD) regimen. Br. J. Haematol., vol. 88(1):94-100 (1994).
Kantarjian et al., Experience with vincristine, doxorubicin, and dexamethasone (VAD) chemotherapy in adults with refractory acute lymphocytic leukemia. Cancer, vol. 64:16-22 (1989).
Kearney et al., Preformulation studies to aid in the development of a ready-to-use injectable solution of the antitumor agent, topotecan. International Journal of Pharmaceutics, vol. 127:229-237 (1996).
Khan et al., Liposome based formulation of SN-38 (LE-SN38): A four-cycle toxicity evaluation in beagle dogs. Toxicological Sciences, vol. 72(S-1):386, Abstract No. 1873 (2003).
Khan et al., A sensitive and rapid liquid chromatography tandem mass spectometry method for quantitative determination of 7-ethyl-10-hydroxycamptothecin (SN-38) in human plasma containing liposome-based SN-38 (LE-SN38). Biomedical Chromatography, vol. 17:493-499 (2003).
King R.E., Remington's Pharmaceutical Sciences, 17th Ed., Mack Publishing Co., Philadelphia, PA, Part 8, Pharmaceutical Preparations and Their Manufacture, pp. 1409-1677 (1985).
Kluin-Nelemans et al., A new non-Hodgkin's B-cell line (DoHH2) with a chromosomal translocation t(14;18) (q32; q21). Leukemia, 5(3):221-224 (1991).
Knight et al., 9-Nitrocamptothecin liposome aerosol treatment of human cancer subcutaneous xenografts and pulmonary cancer metastases in mice. Ann. N.Y. Acad. Sci., vol. 922:151-163 (2000).
Knight et al., Anti-Cancer activity of 9-Nitrocamptothecin liposome aerosol in mice. Transactions of the American and Climatological Association, vol. 111:135-145 (2000).
Knight et al., Anticancer exffect of 9-nitrocamptothecin liposome aerosol on human cancer xenografts in nude mice. Cancer Chemother. Pharmacol., vol. 44:177-186 (1999).
Koshkina et al., Pharmacokinetics and tissue distribution of camptothecin after delivery as a liposome aerosol or following intramuscular

(56) References Cited

OTHER PUBLICATIONS injection in mice. Proceedings of the American Association for Cancer Research, vol. 40:110-111, Abstract No. 734 (1999).

Koshkina et al., 9-Nitrocamptothecin liposome aerosol treatment of melanoma and osteosarcoma lung metastases in mice. Clinical Cancer Research, vol. 6:2876-2880 (2000).

Koshkina et al., Distribution of camptothecin after delivery as a liposome aerosol or following intramuscular injection in mice. Cancer Chemother. Pharmacol., vol. 44:187-192 (1999).

Koshkina et al., Improved respiratory delivery of the anticancer drugs, camptothecin and paclitaxel, with 5% $CO_2$-enriched air: pharmacokinetic studies. Cancer Chemother. Pharmacol., vol. 47:451-456 (2001).

Kruszewski et al., Comparison of the human blood chemistry of free versus liposomal forms of the clinically-relevant topoisomerase I inhibitor Lurtotecan (GI147221). Proceedings of the American Association for Cancer Research, vol. 41:324, Abstract No. 2056 (2000).

Lei et al., Enhanced therapeutic efficacy of a novel liposome-based formulation of SN-38 against human tumor models in SCID mice. Anti-Cancer Drugs, vol. 15:773-778 (2004).

Leonetti et al., Antibody-targeted liposomes containing oligodeoxyribonucleotides complementary to viral RNA selectively inhibit viral replication. Proc. Natl. Acad. Sci. USA 87:2448-2451 (1990).

Lerchen, Hans-Georg, Camptothecin antitumor agents. IDrugs, vol. 2(9):896-906 (1999).

Liu et al., Simple and efficient liposomal encapsulation of topotecan by ammonium sulfate gradient: stability, pharmacokinetic and therapeutic evaluation. Anti-Cancer Drugs, vol. 13:709-717 (2002).

Liu et al., A versatile prodrug approach for liposomal core-loading of water-insoluble camptothecin anticancer drugs. J. Am. Chem. Soc., vol. 124(26):7650-7651 (2002).

Loos et al., Clinical pharmacodynamics of liposomal lurtotecan (NX 211 ): Urinary excretion predicts hematologic toxicity. Proceedings of the American Association for Cancer Research, vol. 42:102, Abstract No. 551 (2001).

Loos et al., Liposomal lurtotecan (NX211 ): determination of total drug levels in human plasma and urine by reversed-phase high-performance liquid chromatography. Journal of Chromatography B, vol. 738:155-163 (2000).

Loos et al., Structural identification and biological activity of 7-methyl-10, 11-ethylenedioxy-20(S)-camptothecin, a photodegradant of lurtotecan Clinical Cancer Research, vol. 8:856-862 (2002).

Lopez-Barcons et al., The novel highly lipophilic topoisomerase I inhibitor DB67 is effective in the treatment of liver metastases of murine CT-26 colorectal carcinoma. Proceedings of the American Association for Cancer Research, vol. 44(2):348, Abstract No. 1782 (2003).

Stewart et al., Cyclophosphamide, doxorubicin, vincristine, and dexamethasone in primay lymphoma of the brain: a case report. Cancer Treatment Reports, 67(3), pp. 287-291 (1983).

Subramanian et al., Liposomal encapsulation increases the activity of the topoisomerase I inhibitor topotecan. Oncology Research, 7(9):461-469 (1995).

Sugarman et al., Liposomal camptothecin: formulation and cytotoxicity against KB cells Proceedings of the American Association for Cancer Research, vol. 34:422, Abstract No. 2519 (1993).

Szoka et al., Comparative properties and methods of preparation of lipid vesicles (liposomes). Ann. Rev. Biophys. Bioeng., vol. 9:467-508 (1980).

Tanyeli et al., Formulation and pharmacological characterization of the novel polyamine camptothecin CT-17 encapsulated in low-clearance liposomes. Proceedings of the American Association for Cancer Research, vol. 42:255-256, Abstract No. 1379 (2001).

Tardi et al., Liposomal encapsulation of topotecan enhances anticancer efficacy in murine and human xenograft models. Cancer Research, vol. 60:3389-3393 (2000).

The Merck Index, Eleventh Edition, Entry Nos. 9887 Vinblastine, 9891 Vincristine, and 9893 Vindoline. Merck & Co., Inc. Rahway, New Jersey, Susan Budavari (Ed.) pp. 1570-1571 (1989).

Thomas et al., Phase 1 multicenter study of vincristine sulfate liposomes injection and dexamethasone in adults with relapsed or refractory acute lymphoblastic leukemia. Cancer, vol. 115(23):5490-5498 (2009).

Thomas, DA et al., Phase II study of liposomal vincristine (Lipov) in relapsed or refractory adult acute lymphoblastic leukemia (ALL). Blood, vol. 94(10, Supp. 1 part 1 of 2):238b, Abstract No. 4269 (1999).

Thompson et al., Animal models for studying the action of topoisomerase I targeted drugs. Biochimica et Biophysica Acta, vol. 1400:301-319 (1998).

Tomkinson et al., In vivo Evaluation of NX 211 in combination with cisplatin, 5-FU and paclitaxel. Proceedings of the American Association for Cancer Research, vol. 41:144, Abstract No. 917 (2000).

Tomkinson et al., Efficacy of NX 211 in SCID mouse models of human leukemia. Proceedings of the American Association for Cancer Research, vol. 42:100, Abstract No. 542 (2001).

Tomkinson et al., OSI-211, a novel liposomal topoisomerase I inhibitor, is active in SCID mouse models of human AML and ALL. Leukemia Research, vol. 27:1039-1050 (2003).

Trosko et al., Mechanism of up-regulatd gap junctional intercellular communication during chemoprevention and chemotherapy of cancer. Mutation Research, 480-481:219-229 (2001).

Ulukan et al., Controlled release of topotecan from thermosensitive liposomes. Proceedings of the American Association for Cancer Research, vol. 36:308, Abstract No. 1833 (1995).

U.S. Appl. No. 08/316,394, filed Sep. 30, 1984.
U.S. Appl. No. 08/481,120, filed Jun. 7, 1995.
U.S. Appl. No. 08/996,783, filed Dec. 23, 1997.
U.S. Appl. No. 11/659,754, filed Feb. 7, 2007.
U.S. Appl. No. 11/880,472, filed Jul. 20, 2007.
U.S. Appl. No. 60/264,616 entitled, Liposomal antineoplastic drugs and uses thereof, Madden, Thomas D. et al. (2001).
U.S. Appl. No. 60/215,556 entitled, Improved liposomal camptothecins and uses thereof, Madden, Thomas D. et al. (2001).

Verschraegen et al., Alternate administration of camptothecin analogues. Ann. N.Y. Acad. Sci., vol. 922:237-246 (2000).

Verschraegen et al., Feasibility, phase I, and pharmacological study of aerosolized liposomal 9-Nitro-20(S)-Camptothecin in patients with advanced malignancies in the lungs. Ann. N.Y. Acad. Sci., vol. 922:352-354 (2000).

Verschraegen et al., Clinical evaluation of the delivery and safety of aerosolized liposomal 9-Nitro-20(S)-Camptothecin in patients with advanced pulmonary malignancies. Clinical Cancer Research, vol. 10:2319-2326 (2004).

Wall et al., Plant antitumor agents. I. The isolation and structure of camptothecin, a novel alkaloidal leukemia and tumor inhibitor from Camptotheca acuminata. J. Am. Chem. Soc., vol. 88(16):3888-3890 (1966).

Waud, Ph.D., William R., Murine L1210 and P388 Leukemias. Anticancer Drug Development Guide: Preclinical Screening, Clinical Trials, and Approval, B. Teicher (Ed.), Humana Press Inc., Totowa, NJ, Chp. 4, pp. 59-74 (1997).

Webb et al., Sphingomyelin-cholesterol liposomes significantly enhance the pharmacokinetic and therapeutic properties of vincristine in murine and human tumour models. British Journal of Cancer, vol. 72:896-904 (1995).

Weereratne et al., Toxicity of sphingomyelin-containing liposomes after chronic injection into mice. Br. J. Exp. Path., vol. 64:670-676 (1983).

Williams et al., Low density lipoprotein receptor-independent hepatic uptake of a synthetic, cholesterol-scavenging lipoprotein: implications for the treatment of receptor-deficient atherosclerosis. Proc. Natl. Acad. Sci. USA 85:242-246 (1988).

Wozniak et al., Randomized trial comparing cisplatin plus vinorelbine in the treatment of advanced non-small cell lung cancer: a southwest oncology group study. J. Clin. Oncol. 16(7):2459-2465, 1998.

(56) References Cited

OTHER PUBLICATIONS

Yu et al., STEALTH liposome formulation enhances antitumor efficacy of CKD-602, a topoisomerase I inhibitor, in human tumor xenograft models. Proc. Amer. Assoc. Cancer Res., vol. 45:710, Abstract No. 3069 (2004).
Zhang et al., Development and characterization of a novel liposome-based formulation of SN-38. International Journal of Pharmaceutics, vol. 270:93-107 (2004).
Zhang et al., A method for determining the encapsulation ratio of camptothecin in polyphase liposome and studies on its leakage property. Acta Pharmaceutica Sinica, vol. 22(12):912-922 (1987).
Zufia et al., Separation methods for camptothecin and related compounds. Journal of Chromatography B, vol. 764:141-159 (2001).
Zunino et al., Camptothecins in clinical development. Expert Opin. Investig. Drugs, vol. 13(3):269-284 (2004).
Zunino et al., Current status and perspectives in the development of camptothecins. Current Pharmaceutical Design, vol. 8:2505-2520 (2002).
Anonymous: Labeling Marqibo, FDA Website Reference ID 3172211, Internet Citation, Aug. 9, 2012, Retrieved from the Internet: URL:http://www.accessdata.fda.gov/drugsatfda_docs/label/2012/202497s000lbl.pdf (retrieved by WIPO on Mar. 10, 2014).
Puscalau Georgeta et al., Reliability of preparation procedure for sphingosomal vincristine. American Journal of Health-Systems Pharmacy, vol. 62, No. 15, pp. 1606-1612 (2005).
International Search Report and Written Opinion for International Application PCT/US2013/071096 filed on Nov. 20, 2013.
International Search Report and Written Opinion for International Application No. PCT/US2016/043622 filed on Jul. 22, 2016.
Gulyakin I.D. i. dr. Osobennocti cozdaniya lekarstvennyh form protivoopuholevyh preparatov dlya parenteralnogo primeneniya. Nauchnoproizvodstvennyi zhurnal, Mai 2015, No. 11, s.1-11. Retrieved from the Internet: http:www.pharmjournal.ru/articles/stati/osobennosti-sozdaniya-lekarstvennyh-form -protivoopuholevyh-preparatov-dlya-parenteralnogo-primeneniya-n11-maj-2015.
Nobel et al., Characterization of highly stable liposomal and immunoliposomal formulations of vincristine and vinblastine. Cancer Chemother. Pharmacol., vol. 64, pp. 741-751 (2009).
Silverman et al., Marqibo (vincristine sulfate liposome injection) improves the pharmacokinetics and pharmacodynamics of vincristine. Cancer Chemother. Pharmacol., 71, pp. 555-564 (2013).
Webb et al., A cationic liposomal vincristine formulation with improved vincristine retention, extended circulation lifetime and increased anti-tumor activity. Letters in Drug Design & Discovery, vol. 4, pp. 426-433 (2007).
Burris, III et al., Activity of topotecan a new topoisomerase I inhibitor, against human tumor colony-forming units in vitro. Journal of the National Cancer Institute, vol. 84(23):1816-1820 (1992).
Chavan et al., A comparative study of the human blood stability characteristics of remote-loaded liposomal carriers containing clinically-relevant camptothecins. Proc. Am. Assoc. Cancer Res., vol. 40:417 Abstract No. 2755 (1999).
Chen et al., Characterization of liposomal mimetic formulations for selective targeting. Proc. Amer. Assoc. Cancer Res., vol. 40:S-161, Abstract No. PT 6019 (1999).
Chen et al., Pharmacokinetic evaluation of liposomal camptothecin. Pharm. Res., vol. 13(9):S-479, Abstract No. PPDM 8345 (1996).
Cheung et al., Loading of doxorubicin into liposomes by forming $Mn^{2+}$-drug complexes. Biochimica et Biophysica Acta, vol. 1414:205-216 (1998).
Chien et al., Cytotoxicity evaluation of a liposome-based formulation of SN38 in human and murine cancer cell lines. Proc. Amer. Assoc. Cancer Res., vol. 44:314, Abstract No. 1607 (2003).
Choice et al., Delivery of topotecan using liposomes: Drug loading into liposomes and drug and carrier pharmacokinetics in female Balb/c mice. Proc. Amer. Assoc. Cancer Res., vol. 40:113, Abstract No. 753 (1999).
Chou et al., Effect of composition on the stability of liposomal Irinotecan prepared by a pH gradient method. Journal of Bioscience and Engineering, vol. 95(4):405-408 (2003).
Chow et al., Liposomal camptothecin and 9-Nitro-Camptothecin: Formulation, pharmacokinetics and preclinical anti-tumor activity. Proceed. Int'l. Syap. Control. Rel. Bioact. Mater., vol. 24:919-920 (1997).
Chow et al., Pharmacokinetics and in vivo antitumor activity of liposomal encapsulated camptothecin and its analog. Proceedings of the American Association for Cancer Research, vol. 38:258, Abstract No. 1733 (1997).
Chow et al., Modified lactone/carboxylate salt equilibria in vivo by liposomal delivery of 9-Nitro-Camptothecin. Ann. N.Y. Acad. Sci., vol. 922:164-174 (2000).
Clements et al., Antiangiogenic potential of camptothecin and topotecan. Cancer Chemother. Pharmacol., vol. 44:411-416 (1999).
Clements et al., Camptothecin exhibits selective cytotoxicity towards human breast carcinoma as compared to normal bovine endothelial cells in vitro.Anti-Cancer Drugs, vol. 7:851-857 (1996).
Colbern et al., Encapsulation of the topoisomerase I inhibitor GL147211C in pegylated (STEALTH) liposomes: Pharmacokinetics and antitumor activity in HT29 colon tumor xenografls. Clinical Cancer Research, vol. 4:3077-3082 (1998).
Corbett et al., In vivo methods for screening and preclinical testing, Use of rodent solid tumors for drug delivery. Anticancer Drug Development Guide: Preclinical Screening, Clinical Trials, and Approval, B. Teicher (Ed.), Humana Press, Totowa, N.J., Chapter 5, pp. 75-99 (1997).
Cortesi et al., Formulation study for the antitumor drug camptothecin: liposomes, micellar solutions and a microemulsion. International Journal of Pharmaceutics, vol. 159:95-103 (1997).
Cortesi et al., Liposomes, micelles and microemulsions as new delivery systems for camptothecin. Eur. J. Pharm. Sci., vol. 6(Suppl. 1):S3, Abstract No. 12 (1998).
Dallavalle et al., Perspectives in camptothecin development. Expert Opinion Ther. Patents, vol. 12 (6):837-844 (2002).
Daoud et al., Multilamellar liposomes as a delivery system for camptothecin (NSC 94600) and 9-aminocamptothecin (NSC 603071). Proceedings of the American Association for Cancer Research, vol. 34:367, Abstract No. 2188 (1993).
Daoud et al., Antitumor effect of liposome-incorporated camptothecin in human malignant xenografts. Anti-Cancer Drugs, vol. 6:83-93 (1995).
Deamer et al., Larger volume liposumes by an ether vaporization method. Biochim. Et Biophys. Acta 443:629-634 (1976).
Desjardins et al., Biodistribution of NX 211, Liposomal GI147211, in tumor bearing mice. Proceedings of the American Association for Cancer Research, vol. 41:702-703, Abstract No. 4467 (2000).
Desjardins et al., Biodistribution of NX211, liposomal lurtotecan, in tumor-bearing mice. Anti-Cancer Drugs, vol. 12:235-245 (2001).
Dumontet et al., Mechanisms of action of and resistance to antitubulin agents: microtubule dynamics, drug transport, and cell death. J. Clin. Onc., 17(3):1061-1070 (1999).
Dunton et al., New Options for the Treatment of Advanced Ovarian Cancer. Seminars in Oncology, vol. 24(1):Suppl. 5:SS-2-SS-11 (1997).
El-Kareh et al., Theoretical models for drug delivery to solid tumors. Critical Reviews in Biomedical Engineering, vol. 25(6):503-571 (1997).
Emerson et al., The topoisomerase I Inhibitor, NX211 demonstrates significant in vivo activity against human acute myeloid leukemia (AML) engrafted in SCID Mice. Blood, Abstract No. 4223 (1999).
Emerson et al., Enhanced in vivo antitumor efficacy of the liposome formulated topoisomerase I inhibitor lurtotecan. Proc. Amer. Assoc. Cancer Res., vol. 40:113, Abstract No. 751 (1999).
Emerson et al., In vivo antitumor efficacy of liposomal lurtotecan (NX211) in human xenografts. Proceedings of the American Association for Cancer Research, vol. 42:100-101, Abstract No. 545 (2001).
Emerson et al., NX-211, a liposomal formulation of lurtotecan demonstrales enhanced pharmacokinetic and antitumor activity. Proceedings of the American Association for Cancer Research, vol. 39:278, Abstract No. 1897 (1998).
Emerson et al., Antitumor efficacy, pharmacokinetics, and biodistribution of NX211: A low-clearance liposomal formulation of lurtotecan. Clinical Cancer Research, vol. 6:2903-2912 (2000).

(56) References Cited

OTHER PUBLICATIONS

Emerson et al., In vivo antitumor activity of two new seven-substituted water-soluble camptothecin analogues. Cancer Research, vol. 55:603-609 (1995).
Emerson, David L., Liposomal delivery of camptothecins. Pharmaceutical Science and Technology Today, vol. 3(6):205-209 (2000).
Erickson-Miller et al., Differential toxicity of camptothecin, topotecan and 9-aminocamptothecin to human, canine, and murine myeloid progenitors (CFU-GM) in vitro. Cancer Chemother. Pharmacol., vol. 39:467-472 (1997).
Fayad et al., Report of a phase II study of sphingosomal vincrsitine (SV) in patients with relapsed or refractory Hodgkin's disease. Journal of Clinical Oncology, vol. 23 (16S) Poster Session 6624 (2005).
Fenske et al., Ionophone-mediated uptake of ciprofloxacin and vincristine into large unilamellar vesicles exhibiting transmembrane ion gradients. Biochim. et. Biophys. Acta 1414:188-204, 1998.
Foley et al., The encephalopathy of chronic renal failure in children. Annals of Neurology, vol. 2(3):254 (1977).
Fraley et al., Entrapment of bacterial plasmid in phospholipid vesicles: potential for gene transfer. Proc. Natl. Acad. Sci. USA, 76(7):3348-3352 (1979).
Gabr et al., Cellular pharmacokinetics and cytotoxicity of camptothecin and topotecan at normal and acidic pHI. Cancer Research, vol. 57:4811-4816 (1997).
Garcia-Carbonero et al., Current perspectives on the clinical experience, pharmacology, and continued development of the camptothecins. Clinical Cancer Research, vol. 8:641-661 (2002).
Gelmon et al., A phase 1 study of OSI-211 given as an intravenous infusion days 1,2, and 3 every three weeks in patients with solid cancers. Investigational New Drugs, vol. 22:263-275 (2004).
Gelmon et al., Phase 1 Study of the NX211 (liposomal lurtotecan) given as an intravenous infusion on Days 1, 2, & 3 every 3 Weeks in patients (pts) with solid tumors—An NCIC Clinical Trials Group Study. Proceedings of the American Association for Cancer Research, vol. 41:610, Abstract No. 3879 (2000).
Gilbert et al., 9-Nitrocamptothecin liposome aerosol: lack of subacute toxicity in dogs. Inhalation Toxicology, vol. 14:185-197 (2002).
Giles et al., Phase I and pharmacokinetic study of a low-clearance, unilamellar liposomal formulation of lurtotecan, a topoisomerase 1 inhibitor, in patients with advanced leukemia. Cancer, vol. 100(7):1449-1458 (2004).
Giles et al., Phase I and pharmacokinetic study of OSI-211, a liposomal formulation of lurtotecan, a topoisomerase I inhibitor, in patients with advanced leukemia. Blood, p. 251 b, Abstract No. 4732 (2003).
Gong et al., Improved lactone stability of 9-nitro-camptothecin in vitro and in vivo by liposomal formulation. Proceedings of the American Association for Cancer Research, vol. 39:430, Abstract No. 2926 (1998).
Gong et al., Sustained organ exposure to 9-nitro-camptothecin (9NC) lactone form by liposomal delivery. Proceedings of the American Association for Cancer Research, vol. 40:417, Abstract No. 2756 (1999).
Gong et al., Development and characterization of liposomal formulation of 9-Nitrocamptothecin. Pharm. Res., vol. 13:S162, Abstract No. PT 6021 (1996).
Green et al., Axonal transport disturbances in vincristine-induced peripheral neuropathy. Ann. Neural., vol. 1(3):255-262 (1977).
Grit et al., Chemical stability of liposomes: implications for their physical stability. Chemistry and Physics of Lipids, vol. 64:3-18 (1993).
Abraham et al., An evaluation of transmembrane ion gradient-mediated encapsulation of topotecan within liposomes. Journal of Controlled Release, vol. 96:449-461 (2004).
Alekseevak, et al., Use of dexamethasone in treatment of high- and low-grade non-Hodgkin's lymphoma. Vopr. Onkol., vol. 50(6):726-728 (2004).

Allen et al., Chronic liposome administration in mice: Effects on reticuloendothelial function and tissue distribution. The Journal of Pharmacology and Experimental Therapeutics, vol. 229(1):267-275 (1984).
Allen et al., Large unilamellar liposomes with low uptake into the reticuloendothelial system. FEBS Letters, vol. 223(1):42-46 (1987).
Allen et al., Liposomes containing synthetic lipid derivatives of poly(ethylene glycol) show prolonged circulation half-lives in vivo. Biochimica et Biophysica Acta, vol. 1066:29-36 (1991).
Allen et al., Liver pathology accompanying chronic liposome administration in mouse. Research Communications in Chemical Pathology and Pharmacology, vol. 50(2):281-290 (1985).
Allen et al., Pharmacokinetics of stealth versus conventional liposomes: effect of dose. Biochimica et Biophysica Acta, vol. 1068:133-141 (1991).
Allen et al., Subcutaneous administration of liposomes: a comparison with the intravenous and intraperitoneal routes of injection. Biochimica et Biophysica Acta, vol. 1150(1):9-16 (1993).
Allen et al., Liposomes with prolonged circulation times: factors affecting uptake by reticuloendothelial and other tissues. Biochimica et Biophysica Acta, vol. 981:27-35 (1989).
Apostolidou et al., Phase I study of OSI-211, a novel liposomal topoisomerase 1 (Topo 1) inhibitor, in patients with refractory leukemia. Blood, Abstract No. 4575 (2002).
Bedikian et al., A pilot study with vincristine sulfate liposome infusion in patients with metastatic melanoma. Melanoma Research, vol. 18(6), pp. 400-404 (2008).
Begu et al., Spectrofluorimetry study of interaction of camptothecin with liposomal bilayer. Luminescence, vol. 15:78-79 (Abstract) (2000).
Belgaumi et al., Dexamethasone-associated toxicity during induction chemotherapy for childhood acute lymphoblastic leukemia is augmented by concurrent use of danunomycin. Cancer 97(11), pp. 2898-2903, 2003.
Bell et al., Topoisomerase I (Topo-1) modulation by liposomal GI147211 (NX211 ). Proc. Amer. Assoc. Cancer Res., vol. 41:773, Abstract No. 4915 (2000).
Bevins et al., Tumor cell cycle disruption and apoptosis induced by DB-67, a highly lipophilic camptothecin displaying improved human blood stability. Proceedings of the American Association for Cancer Research, vol. 42:102, Abstract No. 554 (2001).
Biloti et al., Lipid membrane with low proton permeability. Biochimica et Biophysica Acta, vol. 1611:1-4 (2003).
Bloomfield, V., Quasi-elastic light scattering application in biochemistry and biology. Ann. Rev. Biophys. Bioeng. 10:421-450, 1981.
Bom et al., The highly lipophilic DNA topoisomerase I inhibitor DB-67 displays elevated lactone levels in human blood and potent anticancer activity. Journal of Controlled Release, vol. 74:325-333 (2001).
Bom et al., The structural basis of camptothecin loading and retention in liposomal drug carriers. Proceedings of the American Association for Cancer Research, vol. 42:374, Abstract No. 2016 (2001).
Bom et al., The novel silatecan 7-tert-butyldimethylsilyl-10-hydroxycamptothecin displays high lipophilicity, improved human blood stability, and potent anticancer activity. J. Med. Chem., vol. 43:3970-3980 (2000).
Boman et al., Liposomal vincristine which exhibits increased drug retention and increased circulation longevity cures mice bearing P388 tumors. Cancer Research, vol. 54:2830-2833 (1994).
Boman et al., Vincristine-induced dermal toxicity is significantly reduced when the drug is given in liposomes. Cancer Chemother. Pharmacol., vol. 37:351-355 (1996).
Bostrom et al., Dexamethasone versus prednisone and daily oral versus weekly intravenous mercaptopurine for patients with standard-risk acute lymphoblastic leukemia: a report from the Children's Cancer Group. Blood, vol. 101(10):3809-3817 (2003).
Burke et al., Development and evaluation of a liposomal formulation of highly lipophilic 7-t-butyldimethylsily-1-10-hydroxy-camptothecin. Proceedings of the American Association for Cancer Research, vol. 40:113, Abstract No. 752 (1999).

(56) References Cited

OTHER PUBLICATIONS

Burke, T.G. et al., "Enhanced Bloodstream Stability and In Vivo Activity of Topotecan Formulated in Liposomes," Pharm. Res., vol. 11(10):S-323, Abstract No. POD 7596 (1994).

Burke et al., Liposomal stabilization of camptothecins. Proceedings of the American Association for Cancer Research, vol. 35:416, Abstract No. 2479 (1994).

Burke et al., A versatile pro-drug approach for the liposomal core loading of camptothecin anticancer drugs. Proceedings of the American Association for Cancer Research, vol. 43:1156, Abstract No. 5731 (2002).

Burke et al., Camptothecin design and delivery approaches for elevating anti-topoisomerase I Activities in vivo. Ann. N.Y. Acad. Sci., vol. 922:36-45 (2000).

Burke et al., Liposomal formulations of camptothecins for cancer treatment. Abstracts of Papers American Chemical Society, In Proceedings of the 208th ACS National Meeting, Abstract No. 50 (1994).

Burke et al., Liposomal stabilization of camptothecin's lactone ring. J. Am. Chem. Soc., vol. 114:8318-8319 (1992).

Burke et al., Liposomal stabilization of the lactone ring of camptothecin anticancer drugs. Pharm. Res., vol. 11(10):S220, Abstract No. PDD 7183 (1994).

Burke et al., Stabilization of topotecan in low pH liposomes composed of distearoylphosphatidylcholine. Journal of Pharmaceutical Sciences, vol. 83(7):967-969 (1994).

Laboratory Research Equipment 2013 Sanquast 2013, 2013, p. 45, Aswan 1-41 55-03 Aluminum Block AB-125, 1-4155-04 Aluminum Block AB-135, 1-4155-05 Aluminum Block AB-155, 1-4155-06 Aluminum Block AB-170, 1-4155-07 Aluminum Block AB-185.

Liposomes, Oct. 21, 2013 (Document provided in Taiwanese. Also, corresponding Taiwanese Office Action and Search Report provided for relevance of subject NPL alleged by Taiwanese Examiner).

Mu et al., Preparation Methods of Liposomes and the Study Development. Sep. 7, 2009. (Document provided in Taiwanese. Also, corresponding Taiwanese Office Action and Search Report provided for relevance of subject NPL alleged by Taiwanese Examiner).

English Translation of Taiwanese Office Action and Search Report in counterpart Taiwanese Patent Application No. 105123037, dated Apr. 9, 2018.

Extended European Search Report for European Patent Application No. 18209291.6, dated Mar. 18, 2019.

Park et al., Anti-HER2 Immunoliposomes: Enhanced efficacy attributable to targeted delivery. Clinical Cancer Research, vol. 8, pp. 1172-1181 (2002).

Lasic et al., Gelation of liposome interior: A novel method for drug encapsulation. FEBS, vol. 312, No. 2, 3, pp. 255-258 (1992).

Haran et al., Transmembrane ammonium sulfate gradients in liposomes produce efficient and stable entrapment of amphipathic weak bases. Biochimica et Biophysica Acta, 1151:201-215 (1993).

Mamot et al., Epidermal growth factor receptor-targeted immunoliposomes significantly enhance the efficacy of multiple anticancer drugs in vivo. Cancer Res, 65(24):11631-11638 (2005).

Drummond et al., Optimizing liposomes for delivery of chemotherapeutic agents to solid tumors Pharmacological Reviews, 51(4):691-742 (1999).

* cited by examiner

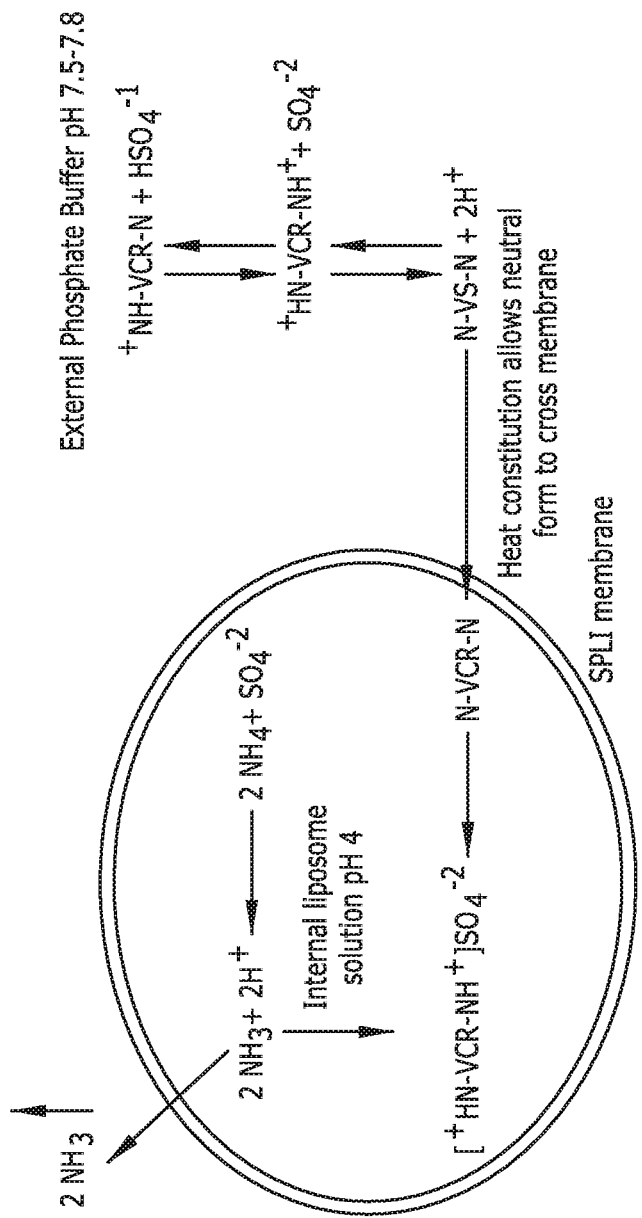

READY-TO-USE FORMULATION FOR VINCRISTINE SULFATE LIPOSOME INJECTION

CROSS REFERENCE TO RELATED APPLICATION

This application is a 371 of PCT/US2016/043622, filed Jul. 22, 2016, which claims benefit under 35 U.S.C. § 119(e) from U.S. Provisional Patent Application Ser. No. 62/195,711, filed Jul. 22, 2015, the contents of which are incorporated herein by reference in their entirety.

BACKGROUND

Liposome formulations of chemotherapeutic agents, like vincristine, may provide significant anti-cancer clinical benefit over their non-encapsulated forms. Pharmaceutical nanoparticle formulations may allow extended drug retention in vivo, longer pharmacokinetic half-lives, and increased accumulation at tumor sites, which may translate into improved clinical outcomes. These characteristics may be particularly attractive for cell cycle specific drugs like Vincristine, which disrupts tubulin binding during cell mitosis. The dramatic liposomal derived advantage is highlighted in the ability to potentially administer Vincristine Sulfate Liposome Injection (VSLI) without a dose cap and may even allow dose intensification. Whereas non-encapsulated vincristine may be prescribed with a dose cap to avoid serious dose limiting neuropathogical toxicities.

The efficacy of the liposomal formulation seems to lie in the ability of the liposome to retain the therapeutic agent and maintain the chemical stability of the active agent. It is thought that when liposomes composed of sphingomyelin-cholesterol are used, as in VSLI, these hydrolysis resistant liposomes allow therapeutically meaningful drug retention times. However, the chemical instability of vincristine can limit the shelf-life stability of VSLI. Stability studies for Marqibo® seem to show that VSLI degradation occurred within 24 hours of constitution at room temperature. The current approved FDA label calls for administration within 24 hrs following constitution. As a result of the long term stability limitations seen with VSLI, it is prepared in the pharmacy just prior to administration.

As a result of the inability to achieve a nominally stable ready-to-use formulation, Vincristine Sulfate Liposomes Injection (0.16 mg/mL) (VSLI) is constituted at the pharmacy from three drug product components supplied as part of the Marqibo® Kit. The three drug product components are Vincristine Sulfate Injection, USP, (VSI), Sphingomyelin Cholesterol Liposome Injection (SCLI), and Sodium Phosphate Injection (SPI). The three component kit was selected as a way to provide a presentation with a shelf life suitable for at least 24 months. The Kit's stability may be governed by the Kit component with the shortest expiry dating at 2-8° C., e.g., vincristine sulfate injection.

It may therefore be desirable to develop a ready-to-use formulation to avoid the need for multi-step compounding at the pharmacy; this would enhance the ease of Marqibo administration, and eliminate the need to procure ancillary equipment, e.g., constitution water bath, and minimize the potential for medicament preparation errors. The product's stability is limited by the degradation of vincristine, principally the formation of N-desformylvincristine (NFV). This appears to be the largest single degradant of VSLI and also VSI, the component of the Marqibo Kit. The increase of this impurity over time leads to both the Marqibo Kit and VSI having an expiration date of 24 months.

Vincristine is a dimeric indoledihydroindole compound isolated from the leaves of the plant *Vinca rosea*. The alkaloid is composed of a N-desmethyl-N-formyl-vindoline moiety bridged to a velbanamine species. It seems to be most stable in its salt form. Salts are easily prepared by adding a theoretical amount of acid to a solution of the alkaloid freebase, however as noted above even vincristine salts have limited stability; 24 months at 4° C. N-deformylation of vincristine sulfate is the prominent degradation pathway of vincristine. The N-formamide is positioned on the N1 nitrogen of a strained vindoline heterocycle and likely distends the amide's carbonyl function into a position vulnerable to either nucleophilic attack or hydrolysis. Other minor degradation pathways include hydrolytic transformations of vincristine such as 4-deacetylation or loss of the methyl ester at 18' followed by decarboxylation.

This lability of vincristine has hampered the development of stable unencapsulated vincristine formulations going back to the VSI USP innovator, Eli Lilly. Lilly sought to develop a freeze dried or lyophilized formulation of vincristine sulfate injection. Vincristine degradation appears to have led to the abandonment of these presentations in favor of a ready-to-use solution containing vincristine sulfate. Vincristine is sensitive to thermal, acid, and photo stress which leads to degradation to the N-desformylvincristine species as well as other related substance impurities. Air oxidation may be a contributor and it has been shown that heat sterilization is not compatible with VSLI or VSI, due to the formation of degradation impurities.

The structural complexity of vincristine and the dimmer's often unpredictable chemical sensitivity has been a bane for the use of common types of excipients typically for pharmaceutical formulations. Eli Lilly scientists noted in their formulation development of VSI the presence of chloride ion should be minimized since it could have "deleterious effects on oncolytic vinca dimers". Deleterious efforts of chloride ions in drug formulations are rare. Sodium chloride is extensively used in pharmaceutical formulations to provide desired isotonic properties. One report claims Doxorubicin and Vincristine both degrade rapidly in 0.45% aqueous sodium chloride and Ringers admixtures at 25° C. to 37° C. The chloride ion has also been implicated in the instability of Thimerosal, an antifungal, in ophthalmic formulations containing sodium chloride as an isotonic agent. These observations highlight the unique and extreme chemical sensitivity of vincristine.

The failure to find a ready-to-use formulation for Marqibo® capable of extended storage resulted in a search for an alternative way to administer VSLI leading to the development of the three vial kit. The three vial constitution process for administration of Marqibo® (with constitution at a pharmacy) received marketing approval from the FDA in August 2012.

Development of a ready-to-use presentation would be a significant improvement for Marqibo® administration. Studies were proposed by Inex, Marqibo innovator, to improve the stability of the VSLI formulation which used lyophilization, ionophore loading, and/or manganese or magnesium sulfate liposome loading platforms. These suggestions were based on using second generation encapsulation methods that were alleged to be milder or electroneutral toward the liposome compared to the pH gradient method. However, no stable ready-to-use formulation was ever achieved during the development of Marqibo. There continues to be a need for a ready-to-use formulation of VSLI.

SUMMARY

Some embodiments include a ready-to-use vincristine composition comprising: a continuous aqueous phase comprising a first aqueous buffer, a liposome phase dispersed within the first aqueous buffer, and a stabilizing aqueous solution encapsulated as cargo within the liposome phase; wherein the stabilizing aqueous solution comprises a second aqueous buffer and stabilized vincristine dissolved therein; wherein the second aqueous buffer comprises a salt having at least one solute that can transport out of the liposome phase and leave a positively charged solute or hydronium ion in the stabilizing aqueous solution, wherein the positively charged solute or hydronium ion stabilizes the vincristine; and wherein the continuous aqueous phase and the stabilizing aqueous solution have a pH difference of at least 2 pH units.

Some embodiments include a method of stabilizing vincristine in a liposome comprising: dispersing a liposome phase within a continuous aqueous phase comprising a first aqueous buffer; wherein the liposome phase contains a stabilizing aqueous solution encapsulated within the liposome phase; wherein the stabilizing aqueous solution comprises a second aqueous buffer and stabilized vincristine dissolved therein; wherein the second aqueous buffer comprises a salt having at least one solute that can transport out of the liposome phase and leave a positively charged solute or hydronium ion in the stabilizing aqueous solution, wherein the positively charged solute or hydronium ion stabilizes the vincristine; and wherein the continuous aqueous phase and the stabilizing aqueous solution have a pH difference of at least 2 pH units.

Some embodiments include methods of treating cancer in a mammal comprising administering a therapeutic amount of a composition comprising, a continuous aqueous phase comprising a first aqueous buffer, a liposome phase dispersed within the first aqueous buffer, and a stabilizing aqueous solution encapsulated as cargo within the liposome phase; wherein the stabilizing aqueous solution comprises a second aqueous buffer and stabilized vincristine dissolved therein; wherein the second aqueous buffer comprises a salt having at least one solute that can transport out of the liposome phase and leave a positively charged solute or hydronium ion in the stabilizing aqueous solution, wherein the positively charged solute or hydronium ion stabilizes the vincristine; and wherein the continuous aqueous phase and the stabilizing aqueous solution have a pH difference of at least 2 pH units.

BRIEF DESCRIPTION OF THE DRAWINGS

FIG. 1 is a representation of an encapsulation mechanism for the vincristine sulfate liposome formulation.

DETAILED DESCRIPTION

Disclosed herein are compositions and methods related to a ready-to-use formulation for vincristine sulfate liposome injection with enhanced stability. Some embodiments were achieved by replacing the citric acid buffer used in the current VSLI formulation with an ammonium sulfate buffer (AS) and creating a multiplex of liposome membrane pH equilibria that increases the concentration of the stable vincristine sulfate species (see FIG. 1). The ammonium sulfate coupled with a complementary external pH buffer may mitigate the degradation of vincristine to N-desformylvincristine while maintaining the structural and dynamic integrity of the sphingomyelin-cholesterol liposome. This may allow efficient loading and retention of vincristine via a transmembrane method. Some embodiments are related to methods for treating various types of lymphomas, such as methods for treating relapsed forms of non-Hodgkin's Lymphoma. Typically, a ready-to-use composition for stabilizing a drug according to this disclosure, can include a continuous aqueous phase, a liposome phase dispersed in the continuous aqueous phase, and a stabilizing aqueous solution encapsulated as cargo within the liposome phase.

A continuous aqueous phase can comprise a first aqueous buffer. The first buffer can stabilize vincristine, and can help facilitate encapsulation of vincristine. For example, a neutral or high pH continuous aqueous phase, such as the external phosphate buffer depicted in FIG. 1, can allow the vincristine to cross the liposome membrane in primarily free base form. By contrast, the stabilizing aqueous solution encapsulated in the liposome has a sufficiently low pH to drive the acid-base equilibrium of vincristine so that the amount of neutral vincristine within the liposome is negligible. For example, this is illustrated by the equilibrium between vincristine free base, vincristine sulfate, ammonia, and ammonium sulfate depicted in the internal liposome solution of FIG. 1. This can provide a concentration gradient of vincristine free base between the continuous aqueous phase, which can have a higher vincristine free base concentration, and the stabilizing aqueous solution encapsulated within the liposome, which can have a negligible vincristine free base concentration. This concentration gradient can drive the migration of free vincristine from the continuous aqueous phase having a high concentration of vincristine free base to the stabilizing aqueous solution within the liposomes, which has a negligible concentration of neutral vincristine. The vincristine loading is also believed to be driven because the salt form of vincristine does not typically pass through the liposome barrier to the continuous aqueous phase, but neutral vincristine can pass through the liposome barrier to the stabilizing aqueous solution within the liposome.

In some embodiments, the first aqueous buffer solution includes any buffer that can buffer the continuous aqueous phase to a pH that provides primarily neutral vincristine, such as but not limited to a salt, an acid or base combined with a conjugate of an acid or a base such as, a monoanionic conjugate base, a dianionic conjugate base, a trianionic conjugate base, a conjugate base, a conjugate acid, or any mixture or combination thereof. In some embodiments, any combination of the above may exist in a titrated mixture. In some embodiments the buffer is a sulfate buffer. In some embodiments, the buffer is a phosphate buffer (e.g., a sodium phosphate buffer), a bicarbonate buffer, a borate buffer, etc. In some embodiments, the first aqueous buffer solution can be the primary carrier solvent or the fluid carrier of the liposome phase.

The first aqueous buffer may be present at any suitable concentration. For example, the first aqueous buffer may be present at a concentration that makes the buffer approximately isotonic, such as a concentration of about 150 mM to about 400 mM or about 250 mM to about 350 mM.

A liposome includes at least the broadest meaning understood by one of ordinary skill in the art and also includes vesicles or nanoparticles composed of a lamellar phase bilayer, such as a lipid bilayer. In some embodiments, a liposome or liposomal layer is formed by any substance that is substantially insoluble in the first aqueous buffer solution including any material known in the art to form liposome nanoparticles. In some embodiments, liposomes comprise any material that may form a vesicle composed of a lamellar phase lipid bilayer. Liposomes may comprise lipids such as phospholipids (e.g., phosphatidylcholines), sphingolipids (e.g., sphingomyelin), glycolipids, phosphoglycerides, polyethylene glycol, cholesterol, etc. In some embodiments, the liposomes comprise pegylated and/or unpegylayted phosphatidyl choline lipids and/or phospholipids. In some embodiments, a lipid component of some liposomes comprises any fatty acid tail that may give useful properties to the lipid bilayer of the liposome, e.g., improved elasticity, improved drug loading, etc.

In some embodiments, the nanoparticle or liposome is used to create a solvent barrier or to create a chemical or osmotic gradient. The liposome or nanoparticle may be used to separate two aqueous solutions of substantially different pH. The nanoparticle may also be used to separate two aqueous solutions of substantially the same pH. In some embodiments, the nanoparticle is used to separate two solutions comprising substantially different buffers. The liposome or nanoparticle may also be used to separate two solutions comprising substantially similar buffers. In some embodiments, the liposome is used to separate two aqueous solutions of both substantially different pH and comprising substantially different buffer solutions. In some embodiments, the gradient formed by the separation of the two aqueous solutions may increase the loading efficiency of the liposome or nanoparticle. In some embodiments, the layer formed by the liposome is described as a liposome phase, liposomal phase, or internal nanoparticle phase.

Encapsulated cargo should be understood to include at least the broadest meaning understood by a person of ordinary skill in the art and includes an aqueous phase that is separated from the surrounding aqueous phase by a liposomal lipid bilayer.

In some embodiments, the liposome encapsulates a stabilizing aqueous solution that may comprise a second aqueous buffer and stabilized vincristine dissolved therein.

In some embodiments, the second aqueous buffer comprises any buffer that can buffer the pH of the stabilizing aqueous solution that comprises an ammonium salt, e.g., an ammonium sulfate buffer, an ammonium citrate buffer, an ammonium phosphate buffer, an ammonium bicarbonate buffer, an ammonium carbonate buffer, an ammonium borate buffer, etc. It is believed that an ammonium buffer can help to stabilize the vincristine by maintaining the stabilizing aqueous solution at a lower pH over time as compared to other buffers that initially provide a similar pH. It is believed that non-ammonium buffers can lose their buffering capacity over time. Once a drug is encapsulated in the liposome, it may become highly concentrated in the liposome, creating complex ion migration equilibria, which if not balanced may contribute to the degradation of vincristine. Unexpectedly, ammonium buffers can maintain a more stable pH than other buffers with initially similar pH. This may be because, for systems such as the one depicted in FIG. 1, free ammonia can escape through the liposomal barrier leaving behind a proton which thereby stabilizes the internal liposome pH.

In some embodiments, the stabilized therapeutically active agent is any medicament that can be stabilized in the stabilizing aqueous solution. In some embodiments, the stabilized therapeutically active agent is an anticancer drug such as but not limited to vincristine.

Vincristine may be represented by the following chemical structural formula:

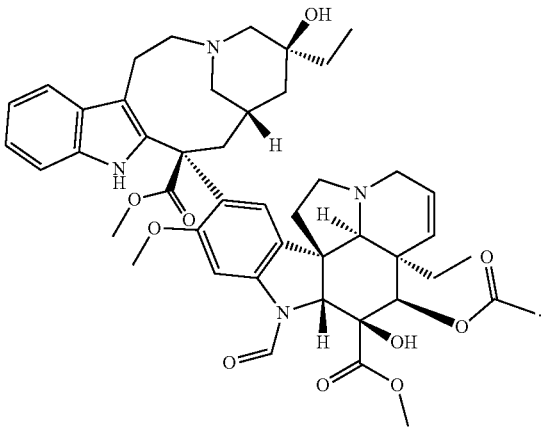

Vincristine may also be represented by the chemical name: (3aR,3a¹R,4R,5S,5aR,10bR)-methyl-4-acetoxy-3a-ethyl-9-((5S,7S,9S)-5-ethyl-5-hydroxy-9-(methoxycarbonyl)-2,4,5,6,7,8,9,10-octahydro-1H-3,7-methano[1] azacycloundecino[5,4-b]indol-9-yl)-6-formyl-5-hydroxy-8-methoxy-3a,3a1,4,5,5a,6,11,12-octahydro-1H-indolizino[8,1-cd]carbazole-5-carboxylate.

In some embodiments, the second aqueous buffer solution helps to stabilize the vincristine dissolved within the stabilizing aqueous solution. In some embodiments, a therapeutically active agent is substantially more stable in the stabilizing aqueous solution than it would be in the first aqueous buffer. In some embodiments, vincristine is substantially more stable in the stabilizing aqueous solution than in the first aqueous buffer.

The stabilizing aqueous solution comprises a second aqueous buffer. The second aqueous buffer should comprise a salt having at least one solute that can transport out of the liposome phase. When the solute transports out of the liposome phase, it leaves a positively charged solute or hydronium ion in the stabilizing aqueous solution. Thus, the positively charged solute or hydronium ion can stabilize the vincristine. There are a number of salts that can transport out of the liposome phase and leave behind a positively charged solute or hydronium ion. For example, charge neutral bases can transport out of liposome phases. Thus, for a salt of a neutral base, such as ammonia, amines, amino acids, phosphines, etc., the neutral base, e.g. ammonia or an amine, can transport out of the liposome phase, and the cation or hydronium ion from the salt can remain in the stabilizing aqueous solution. Examples of suitable stabilizing salts can include, but are not limited to, salts of ammonia, or salts of amines, such as methylamine, dimethylamine, trimethylamine, ethylamine, diethyl amine, triethylamine, ethanolamine, diethanol amine, triethanol amine, etc.

In some embodiments, the therapeutically active agent is substantially stabilized by an ammonium salt in the second aqueous buffer. In some embodiments, an ammonium sulfate buffer substantially reduces the rate of degradation of vincristine to desformylvincristine. In some embodiments, ammonium sulfate substantially protects vincristine against deformylation. In some embodiments, the presence of ammonium ion may substantially protect vincristine against deformylation. In some embodiments, the primary contributor of the ammonium ion to the solution is ammonium sulfate. In some embodiments, any ammonium salt buffer may contribute to protecting vincristine against deformylation.

The second aqueous buffer may be present in the stabilizing aqueous solution at a pH that may help to stabilize the vincristine. In some embodiments, the second aqueous buffer, such as an ammonium salt, e.g. ammonium sulfate, may be present The composition of claim 1, wherein the ammonium salt is present in the second aqueous buffer at a concentration of about 100 mM to about 500 mM, about 200 mM to about 400 mM, about 200 mM to about 300 mM, about 250 mM to about 300 mM, about 300 mM to about 350 mM, or about 250 mM to about 350 mM.

In some embodiments, the continuous aqueous phase or the first aqueous buffer has a pH of from about pH 5 to about pH 8.8 or about pH 9, from about pH 5 to about pH 6, from about pH 6 to about pH 7, from about pH 7 to about pH 8, from about pH 7 to about pH 8.5, from about pH 7 to about pH 8.8 or about pH 9, from about pH 7.2 to about pH 7.8, from about pH 7.4 to about pH 7.8, from about pH 7.8 to about pH 8, from about pH 8 to about pH 8.2, from about pH 8.2 to about pH 8.8, from about pH 8.4 to about pH 8.8, about pH 7.8, about pH 7.4, about pH 8, or any pH bounded by or between any of these values.

In some embodiments, the stabilizing aqueous solution or the second aqueous buffer has a pH from about pH 3 to about pH 5.5, from about pH 3 to about pH 4, from about pH 3.5 to about pH 4.5, from about pH 4 to about pH 5, about pH 4, or any pH bounded by or between any of these values.

In some embodiments, the pH difference or ΔpH between the continuous aqueous phase and the stabilizing aqueous solution or the first aqueous buffer and the second aqueous buffer is from about 1 pH unit to about 4 pH units, from about 2 pH units to about 3 pH units, from about 1.5 pH units to about 2.5 pH units, from about 2.5 to about 3.5 pH units, from about 3 pH units to about 4 pH units, about 3.8 pH units, or any difference bounded by or between any of these values.

In some embodiments, the ΔpH may help to increase the liposome encapsulation efficiency. In some embodiments a ΔpH useful to achieve useful liposome loading is from about 1 pH unit to about 4 pH units, from about 2 pH units to about 3 pH units, from about 1.5 pH units to about 2.5 pH units, from about 2.5 pH units to about 3.5 pH units, from about 3 pH units to about 4 pH units, about 3.8 pH units, or any difference bounded by or between any of these values.

In some embodiments, the loading of the liposome with active ingredient may be described as transmembrane potential loading. In some embodiments the potential is created by the proton gradient as described above, which leads to accumulation of the therapeutic agent inside of the liposome.

In some embodiments, the combination of the ΔpH, the buffers employed, and the liposome results in a balance of both the characteristics needed for good loading of the therapeutically active agent and the characteristics that minimize degradation of the therapeutically active agent.

In some embodiments, the disclosed composition includes an ammonium sulfate buffer which may create a multiplex of liposome membrane pH equilibria that results in an increased concentration of the stable vincristine sulfate species (see FIG. 1). The disclosed liposome formulation's use of the ammonium sulfate equilibria coupled with ion migration control by a complementary external pH buffer surprisingly mitigates the degradation of vincristine to N-desformylvincristine (NFV), yet maintains the structural and dynamic integrity of the liposome to allow efficient loading and retention of vincristine via a transmembrane method.

N-desformylvincristine may be represented by the structural formula:

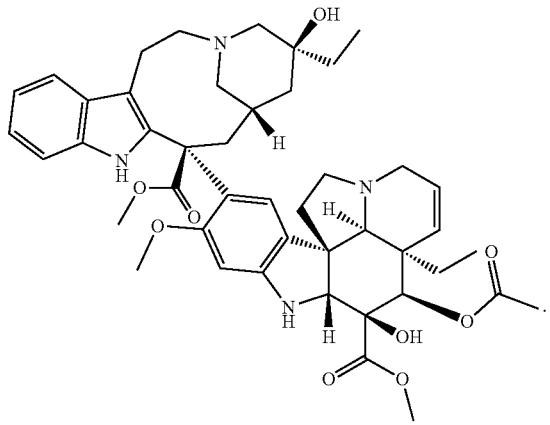

N-desformylvincristine may also be represented by the chemical name, (3aR,3a$^1$R,4R,5S,5aR,10bS)-methyl 4-acetoxy-3a-ethyl-9-((5S,7S,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-3a,3a1,4,5,5a,6,11,12-octahydro-1H-indolizino[8,1-cd]carbazole-5-carboxylate.

NFV may sometimes be formed even when a gradient exists (i.e., pH 4 interior and pH 7.5 exterior) or if the external and interior pH is the same (i.e., pH 4). This may imply that vincristine species, which may be susceptible to the irreversible deformylation reaction, may be formed inside the liposome. One possible species is neutral vincristine, which may be susceptible to vincristine degradation pathways. One advantage of the presently disclosed compositions is their ability to minimize the formation of vincristine species susceptible to degradation within the liposome.

In some embodiments, the compositions disclosed herein can be administered to a mammal for the treatment of cancer or for the treatment of relapsed cancer. In some embodiments, the cancer includes lymphoma or leukemia. In some embodiments, the mammal may have previously undergone cancer treatment therapy.

In some embodiments, the compositions disclosed herein can be included in methods for the treatment of a neoplasia in a mammal. In some embodiments, the compositions disclosed herein can be included in methods for the treatment of relapse forms of a neoplasia in a mammal. In some embodiments, the composition disclosed herein can be included in a method for the treatment of various types of lymphomas. In some embodiments, the composition disclosed herein can be administered for the treatment of non-Hodgkin's Lymphoma. In some embodiments, the composition disclosed herein can be administered for the treatment of the relapse of non-Hodgkin's Lymphoma.

The term neoplasia, as used herein, includes at least the broadest meaning understood by a person of ordinary skill in the art and also includes any aberrant growth of cells, tumors, malignant effusions, cysts, etc. A cite of neoplasia can contain a variety of cell types, including without limitation, neoplastic cells, endothelial cells, or immunological cells such as leukocytes, myelocytes, lymphocytes, etc.

In some embodiments, the neoplasia to be treated is a cancer.

In some embodiments where the composition is vincristine sulfate liposome injection (VLSI), the composition can be administered to a mammal for the treatment of cancer, or relapsed cancer. The composition can be administered at a dose of from about 1 mg/m$^2$ to about 4 mg/m$^2$, about 1.5 mg/m$^2$ to about 3 mg/m$^2$, about 2 mg/m$^2$ to about 3 mg/m$^2$, about 2 mg/m$^2$ to about 2.5 mg/m$^2$, about 2 mg/m$^2$, about 1.5 mg/m$^2$, about 2.25 mg/m$^2$, about 2.5 mg/m$^2$, about 3 mg/m$^2$, about 2.0 mg/m$^2$, about 2.1 mg/m$^2$, about 2.2 mg/m$^2$, about 2.3 mg/m$^2$, about 2.4 mg/m$^2$, or about 1.9 mg/m$^2$. In some embodiments, VLSI is administered in combination with other therapeutic compounds. In some embodiments, VLSI is administered in combination with other anti-neoplastic medicaments.

Example 1: Lower Free Drug Content, Dialyzed Margibo Formulation

The stability of vincristine sulfate liposome injection (VSLI) is reflected in its degradation to N-desformylvincristine (NFV). VSLI when constituted from the 3-vial kit formulation, it may require administration within 24 hours due to the potential degradation of vincristine. The preparation of VSLI also always achieves ≤5% free vincristine. The free vincristine would be in the external pH 7.4 buffer environment. However it is thought that vincristine is most stable in its salt form (pKa 5.0 & 7.4), and at pH 7.4 the equilibria would be less favorable for the salt form compared to the pH 4.0 of the liposome interior. It may be useful to examine to what extent the free vincristine contributed to the formation of NFV and its influence to the overall stability of VSLI.

VSLI was prepared from Marqibo kit equivalent components, i.e., VSI, SPI, and SCLI. Free (unencapsulated) vincristine was removed by dialysis using various buffers under variant pH conditions. The variants were put on stability for up to 12 weeks and assayed for key VSLI stability indicating criteria. The variations examined dialysis using the following external buffers:

a) Phosphate-buffered sucrose solution, pH 7.4
b) Phosphate-buffered saline (PBS) pH 7.4
c) Phosphate-buffered sucrose solutions, pH 4.0
d) Phosphate-buffered sucrose solutions, pH 5.0

Preparation of External Vincristine Free VSLI with pH 4.0-7.4 External Buffer

Three separate VSLI encapsulations from kit components were performed (31 mL each) and pooled. A post-loading sample was removed for analysis and the remaining sample volume divided in four portions (~21.75 mL each). These samples were placed into Spectrapor No. 1, 40 mm width, 6-8 kDa MWCO dialysis membrane bags and dialyzed against 20 volume excess using either phosphate-buffered saline (PBS) or phosphate-buffered sucrose solutions, pH 7.4 for four volume exchanges over a 24-hour period at room temperature protected from light. The PBS prepared contained 20 mM sodium phosphate, 130 mM sodium chloride, pH 7.4. Phosphate-buffered sucrose contained 10% (w/v) sucrose, 20 mM sodium phosphate, pH 7.4. Post dialysis, samples from the same buffer were pooled together, sterile filtered under aseptic conditions using disposable syringe filters (Pall Acrodiscs, 0.2 μm pore size, Supor membranes), and aliquoted into individual, sterile tubes (4.2 mL) for each timepoint of the stability study (0, 2, 4, 8, 12 weeks at 2-8° C.; 2, 4, 8, 12 weeks at room temperature and 2 weeks at 40° C.).

Preparation of External Vincristine Free VSLI with pH 4 and 5 External Buffers

Preliminary Small Scale Evaluations

An initial test study was carried out to ascertain whether dialysis of Marqibo under low pH conditions actually occurred. A total of 8 mL VSLI product was prepared from Marqibo kit vials as described above and the post-loading material was divided into 2 mL aliquots for dialysis in Spectrapor No. 1, 20 mm width, 6-8 kDa MWCO dialysis membrane bags against 20 volume excess using SPI solutions at either pH 4, 5, or 6 for four volume exchanges over a twenty-four hour period at 2-8° C., protected from light. Post-dialysis samples were assayed for free vincristine content (Table 1) and show that dialysis with low pH external buffer is possible.

TABLE 1

Effect of dialysis on total and percent free drug for Marqibo variants.

| Sample | Total Drug (μg/mL) | % Free Drug |
|---|---|---|
| Marqibo post-dialysis at pH 4 | 166.7 | 0.4 |
| Marqibo post-dialysis at pH 5 | 161.7 | 0.2 |
| Marqibo post-dialysis at pH 6 | 165.4 | 0.3 |

Scale up of Dialysis Variants

A 50 mL solution of VSLI product was prepared from a Marqibo kit vials as described in above. The post-loading product volume was divided in two, and each half was placed into Spectrapor No. 1, 40 mm width, 6-8 kDa MWCO dialysis membrane bags and dialyzed against 20 volume excess using phosphate-buffered sucrose solutions at either pH 4 or 5 for four volume exchanges over a seventy-two hour period at 2-8° C. protected from light. Post-dialysis samples were collected, sterile filtered, and aliquoted into individual, sterile tubes (3.5 mL) for each timepoint of the stability study (0, 2, 4, 8, 12 weeks at 2-8° C. and 2, 4 weeks at room temperature).

Stability Analysis Protocol

At each stability time point samples were analyzed for: pH (Beckman Phi 360 pH meter), osmolality (Wescor Inc. Vapro 5520 vapor pressure osmometer), particle size, total and free vincristine, and drug-related impurities.

Results

The stability results of removing free vincristine from the external buffer of VSLI prepared from the 3-vial formulation are shown in Table 2. Removing free vincristine did not appear to improve VSLI stability. Within 4 weeks the NFV had doubled in quantity at 4° C. and by eight weeks the degradation rate was >1.3% NFV/month for all the buffer and pH variants. Total vincristine decreased in parallel to the formation of NFV. VSLI without free external vincristine also followed known vincristine chemical degradation characteristics where the drug degraded more rapidly at room temperature, doubling the percent NFV within 2 weeks. These rates of degradation are similar to the 1.6% NFV/month observed for 3-vial Marqibo kit stability at 4° C. which led to requiring administration of VSLI within 24 hours of constitution, due to the degradation of vincristine to NFV.

The results from these dialysis studies confirm that a stability driver of VSLI is the formation of N-desformylvincristine (NFV). The shelf life of VSLI would be determined by how rapidly NFV would increase to levels outside the 3.0 specification limit. The loss of total vincristine correlated with the observed growth of NFV. Total impurities did not increase disproportionately to the growth of NFV, which is included in the total impurity assignment. No new impurities were observed. All the variants remained within the allowed VSLI criteria for pH, osmolality, and particle size and no trends toward outlying specifications were observed for these criteria. In addition, substitution of sucrose as an isotonic agent for mannitol, which is present in the 3-vial formulation, did not have an effect on the degradation rate of vincristine.

Additionally the results shown in Table 2 demonstrated that removal of free vincristine by dialysis using pH 4 and pH 5 buffers did not alter the integrity of the liposome membrane. Altering the magnitude of the ΔpH gradient did not cause leakage of liposome contents (as might have been expected if the pH-loading gradient had been compromised). Free vincristine remained constantly low in all the variants over time.

TABLE 2

Stability of VSLI Post Dialysis of External Free Drug

| VSLI Variant Buffer | pH | Stability Temp °C. | Stability Time, wks. | % Free Drug | Total % Drug | % NFV | % NFV/ Month |
|---|---|---|---|---|---|---|---|
| PBS | 7.4 | 4 | 12 | 0.10 | 93.0 | 6.4 | 1.3 |
| PBS | 7.4 | RT | 12 | 0.22 | 76.1 | 22.8 | 6.7 |
| Sucrose-PB | 7.4 | 4 | 12 | 0.08 | 93.0 | 6.5 | 1.3 |
| Sucrose-PB | 7.4 | RT | 12 | 0.12 | 76.1 | 22.7 | 6.7 |
| Sucrose-PB | 4.0 | 4 | 4 | 0.23 | 94.6 | 4.8 | 1.3 |
| Sucrose-PB | 4.0 | RT | 4 | 0.37 | 88.6 | 10.3 | 8.1 |
| Sucrose-PB | 5.0 | 4 | 8 | 0.18 | 94.5 | 4.9 | 1.4 |
| Sucrose-PB | 5.0 | RT | 8 | 0.33 | 88.7 | 10.4 | 8.2 |

The results of these dialysis studies demonstrate that free external vincristine degradation does not play a major role in determining of the observed stability of VSLI, although it likely contributes in a minor way to the overall stability of VSLI. These results show that degradation of vincristine is occurring inside the liposome post constitution of VSLI prepared from the 3 vial kit. Maintaining a ΔpH gradient between the inside and outside of the liposome or removing (or minimizing) the ΔpH of VSLI does not improve the stability of Vincristine inside the liposome for the 3 vial formulation.

Example 2: Ammonium Sulfate VCR Liposome Variants

Marqibo is constituted by incubating the Marqibo Kit components (VSI, SCLI, and SPI) together in a pharmacy. Vincristine sulfate, a weak base, is loaded into the liposome by the action of a transmembrane gradient created by the pH differential of the internal SCLI pH 4.0 and the resulting liposome external SPI buffer pH 7.4. During the loading process, only the neutral form of vincristine passes through the liposome membrane and is trapped inside the SCLI as the citrate salt. This loading with citrate buffer provides greater than 95% loading of vincristine. However, once constituted, the internal vincristine citrate is moderately unstable such that within 24 hours the growth of NFV occurs despite the liposome internal pH 4.0, which should maintain vincristine as a salt species. From the earlier free drug dialysis experiments described above the degradation of vincristine appears to be occurring inside the liposome and not from either the external vincristine pH 7.4 environment or vincristine leaking from the liposome. It is conceivable that the citrate buffering capacity in the interior liposome is inefficient and may allow protons and solute ions to migrate across the membrane to an extent that destabilizes the internal pH 4.0 buffer of the liposome. To examine this possibility the liposome interior's sodium citrate buffer was replaced with an alternative "loading battery." A series of experiments were conducted where the internal liposome buffer was ammonium sulfate solution (AS). The pH of 250 mM ammonium sulfate is about 5.5: however, inside the liposome the dissociation equilibrium between ammonia and ammonium salt allows the neutral ammonia molecules to cross the liposome membrane effectively decreasing the internal pH as a result of the hydrogen ions left behind. The resulting internal pH is about 4. This equilibrium may maintain vincristine sulfate as the salt form better than the sodium citrate-citric equilibrium inside the liposome environment of Marqibo. In these experiments the external pH was varied from 5.5 to 8 maintaining an internal pH of about 4.0 (as a result of the ammonia/ammonium equilibrium described above). The molality or buffer capacity were varied between 250 and 350 mM AS, and the isotonic components contributing to overall osmolality was varied using polyols and ionic salts. In all the experiments the liposomes were composed of sphingomyelin and cholesterol essentially in the same composition as SCLI. The only change was the replacement of citrate buffer with ammonium sulfate buffer.

Liposome Preparation Unit Processes.

This example describes the general methods used for sphingomyelin-cholesterol liposome production.

Target Liposome Ingredient Preparation Calculations.

Marqibo liposomal membranes contain sphingomyelin (SM) and cholesterol (CH) in the weight ratio 2.5:1 where the final product VSLI contains 2.37 mg/mL SM.

In these experiments, a target concentration for non-drug loaded liposome variants was chosen at 43 mg/mL SM in order to be easy to process and be sufficiently concentrated for the drug loading step.

The liposome preparation unit processes are as follows: for a target of 70 mL final product:
1. Hydration (Formation of Liposomes)
   Lipid Dissolution.
   SM and CH lipid raw materials are dissolved in ethanol. Sufficient ethanol is used to give a final concentration in the hydrated phase of 15.7% (v/v). In the example above, 3 g SM and 1.2 g CH are weighed and mixed together and dissolved in 13 mL of 200 proof ethanol. Dissolution is achieved by warming the ethanolic lipid mixture in a sealed container at 75° C. until a clear ethanolic solution is obtained.
   Aqueous Hydration.
   The above prepared lipid solution is "hydrated" by rapidly pouring the ethanolic lipid solution into an aqueous phase that has been previously equilibrated to 65° C. in a water bath. In this example, 70 mL of aqueous phase was used containing solutes of interest that will be encapsulated by the liposome formulation. For example, 350 mM ammonium sulfate or related salts. The resulting mixture is incubated for 0.5-1 hour with agitation, to allow the lipids to fully hydrate. When the ethanolic solution of lipids is mixed with the aqueous phase, the ethanol solvent is rapidly diluted, exposing the lipids to water, this results in the lipids spontaneously forming liposomes vesicles with a heterogeneous size distribution. The hydration ensures that water molecules associate completely with the hydrophilic portions of the molecules.

2. Downsizing.

Following the formation of liposomes the vesicles are sized so as to create a population of liposomes having a uniform and preferred particle diameter (in this case about 100 nm). This is achieved by extruding the liposome suspension, created in Step 1 above, through membranes of defined pore size under pressure. Extrusion is performed at 65° C. and passage of the liposomes through the membrane pores is facilitated by the ethanol remaining from hydration. As a result of this treatment, the liposomes conform approximately to the diameter of the membrane pores used. In these studies a Lipex extruder (Northern Lipids) capable of holding 100 mL total volume was used, and the liposome suspension was passed through 25 mm diameter polycarbonate membranes of pore size 0.2 µm (three passes) and 0.08 µm (five passes) using nitrogen gas at pressures of 100-400 psi. (Whatman Nucleopore Track-Etched Membranes). Liposome particle size is measured by a ZetaPALS particle sizer utilizing dynamic light scattering (Brookhaven Instruments Corporation).

3. External Buffer Exchange.

At this stage the external aqueous phase (e.g., 350 mM ammonium sulfate solution) is exchanged for 10% sucrose solution or other desired buffer, such as SPI by dialysis or diafiltration; simultaneously removing ethanol. This process establishes a liposome gradient (i.e., ammonium sulfate buffer inside the liposome and 10% sucrose buffer on the outside of the liposomes). Ammonium sulfate is highly disassociated into ammonium and sulfate ions in the aqueous medium. As charged ions they cannot cross the liposomal membrane, however ammonium ions are also in equilibrium with water and ammonia, which as a neutral gas can cross the liposome membrane. When an ammonia molecule leaves the liposome interior, a proton is left behind; lowering the pH inside the liposomal membrane to about 4. This establishes a $\Delta$pH gradient where the liposome interior is about pH 4.0 and the exterior is the pH of the exchange buffer (e.g., 7.4). This gradient is used to load vincristine into the liposomes. The diafiltration protocol (for product volumes >50 mL) is 15 volume exchanges of buffer using a MidGee cartridge (model UFP-300-E-3MA, 300,000 MWCO) attached to a QuixStand diafiltration system (GE Healthcare Life Sciences). Dialysis (for product volumes <50 mL) consists of placing the liposome suspension into a Spectrum Spectrapore molecular porous membrane with MWCO 6-8000 and suspending it in 20 volumes excess buffer at room temperature, the external buffer is exchanged four times during the course of a day, including one exchange lasting overnight. Following external buffer exchange, the SM content of each post-diafiltration preparation was measured using the Stewart phospholipid choline assay.

4. Drug Loading.

Drug loading is carried out using the VSLI prescribed drug-to-lipid ratio to achieve the desired total volume. The VSLI loading mixture is targeted for 0.16 mg/mL vincristine, 2.37 mg/mL SM (as the liposome preparation), and adjusted to the desired total volume with the external liposome buffer to be used for the desired experimental variant. Loading is carried out by mixing the external buffer, the drug, and the liposome solutions (pre-equilibrated to room temperature), and incubating the mixture for 10 minutes at 65° C. in a water bath for 10 minutes, with gentle mixing. The mixture is then removed from the water bath to cool to room temperature and stored at 2-8° C.

5. Sterile Filtration and Vial Fill

The drug loaded bulk liposome suspension can be sterilized by conventional liposomal sterilization techniques, such as filtration into suitable vials for storage. Aseptic/sterile technique is used throughout and operations performed in a Nunair Class II, type A/B3 Biological Safety Cabinet. Bulk product at room temperature is filtered through sterile 25 mm diameter, 0.2 µm pore-size Acrodisc® syringe filters, Supor® membrane (Pall Corp.) using a sterile, 10 mL syringe with Luer fitting. The bulk is filtered in 10 mL quantities into sterile receiving containers Liposome variant preparations were made by entrapping various molarities of AS as the internal liposome buffer. The liposomes were prepared using the processes described above. The liposomes were prepared with sphingomyelin (SM) and cholesterol (CH) weighed, in duplicate, for a final hydration volume of 70 mL at 43 mg/mL SM and an SM/CH weight ratio 2.5:1. The lipid mixtures were dissolved in 9.5 mL ethanol at 75° C. and hydrated by pouring the ethanolic lipid solution into 70 mL of pre-warmed, 65° C. AS solution and mixing for thirty minutes producing a final ethanol concentration of 12% v/v. The liposomes thus formed were sized by sequential extrusion in a Lipex extruder (Northern Lipids) through polycarbonate membranes of pore size 0.2 µm (three passes) and 0.08 µm (five passes). Following extrusion, each preparation was diafiltered into 10% sucrose solution (simultaneously removing any ethanol) using 15 volume exchanges in a MidGee cartridge (model UFP-300-E-3MA, 300,000 MWCO) and QuixStand holder (GE Healthcare Life Sciences). The SM content of each post-diafiltration preparation was measured using the Stewart phospholipid choline assay.

Small-scale test drug loadings using the above prepared liposomes were carried out using either SPI buffer adjusted to pH 5.5, 6.5 or 7.5 or phosphate-buffered sucrose at pH 5.5, 6.5, or 7.5. Variants loading less than 5% free vincristine were selected for scale up, which were SPI buffer at pH 6.5, 7.5, and phosphate-buffered sucrose at pH 6.5. Larger-scale loadings were performed for each AS variant and buffer following the previously described constitution procedure. The resulting drug encapsulated liposome mixtures were sterile filtered and monitored for stability at 0, 2, 4, 8, 12 weeks at 2-8° C. and 2, 4 weeks at room temperature.

The small-scale ammonium sulfate exploratory experiments described in the experimental section above examined the encapsulation efficiency of AS variants. These results suggest that an ammonium sulfate interior buffer, which leads to an internal liposome pH of approximately 4.0 under equilibrium conditions, is able to load vincristine best when the external buffer pH was 6.5 or greater and without employing a polyol. All variants using an external buffer of pH 5.5 loaded less than 90%; apparently providing an insufficient transmembrane $\Delta$ pH gradient. The PBS buffer variants all loaded at least 95 percent of the drug, while variants which used sucrose had mixed results; showing a wider range of 89-95% encapsulation. Both the 250 mM and 350 mM buffering capacity variants showed similar encapsulation trends with pH and polyol variations. All the variants that showed ≥95% loading were scaled up and evaluated for stability.

The 24-week stability results of the scaled up ammonium sulfate liposomes are summarized in Table 3. All the variants maintained the desired VSLI particle size and osmolality criteria. The pH and percent free vincristine also remained consistent over the stability monitoring period. The ammonium sulfate buffer did not alter the permeability characteristics of the sphingomyelin cholesterol liposome. Improved stability over the 3 vial Marqibo formulation was observed with formulations of 250 mM and 350 mM ammonium sulfate with external PBS buffer pH 7.5. For these variants degradation rates were observed of 0.2 percent NFV per month at refrigerated temperature. This rate could project the formulation's shelf life to be about one year. Additionally the total impurities only increased proportionally with any increase of % NFV. Overall total impurities maintained levels well below the VSLI criteria of less than 6%.

Ammonium sulfate liposomes with an external buffer of pH 6.5 or where the buffer contained a polyol isotonic agent, e.g. sucrose, resulted in inferior stability rates compared to the pH 7.5 variants. Degradation rates for these variants ranged from 1.5-1.8 NFV percent/month at refrigerated temperature (Table 3); rates similar to the VSI component of the current 3-vial citrate based kit formulation (Table 2). Both the 250 mM and 350 mM variants showed the same trends with pH and osmotic agent changes. Additionally, in all cases where the stability was monitored at room temperature rapid vincristine degradation was seen. Only refrigerated samples provided suitable stability characteristics with the ammonium sulfate formulations.

The 250 mM and 350 mM ammonium sulfate vincristine liposomes SPI pH 7.4 formulations display preliminary shelf life requirements suitable for a commercial ready-to-use formulation and were selected for further evaluation.

The results of small scale exploratory experiments are shown on Table 6. Drug-loading results when $Mg^{2+}$ or $Mn^{2+}$ were included in the interior buffer of the liposome and incubated for either 10 (standard condition) or 30 min at 65° C. showed less efficient loading compared to the standard 3-vial kit constitution. The best loading rates of 6-8% free drug were observed with incubations for ten minutes, with the exception of citrate-Mg variant, which showed 21% free drug. The presence of the divalent metal ions appears to result in either disruption of the pH gradient equilibria or collapse of membrane permeability.

TABLE 6

Drug loading for metal ion containing samples.

| Sample | Load 10 min, % free drug | Load 30 min, % free drug |
| --- | --- | --- |
| Marqibo (control, 2 mL) | 1 | 2 |
| AS/$Mg^{2+}$ | 6 | 52 |
| AS/$Mn^{2+}$ | 7 | 55 |
| Cit/$Mg^{2+}$ | 21 | 80 |
| Cit/$Mn^{2+}$ | 8 | 54 |

The ammonium sulfate with $MgSO_4$ variant, which showed 6% free drug after loading, was scaled up and monitored for stability. On scale-up this formulation variant

TABLE 3

Summary of Ammonium Sulfate Liposome Formulation Variant's Stability at 4° C.

| Internal Liposome content/external buffer | mM | pH | Stability Temp ° C. | Stability Time (wks) | Part size (nm) | Osmolality (mmol/kg) | Total VS (mg/mL) | % Free | % NFV | % Total Imp | % NFV/Mo |
| --- | --- | --- | --- | --- | --- | --- | --- | --- | --- | --- | --- |
| AS/SPI | 250 | 6.5 | 4 | 24 | 93 | 543 | 159.88 | 1.22 | 11.15 | 11.87 | 1.47 |
| AS/SPI | 250 | 7.5 | 4 | 24 | 94 | 550 | 176.75 | 2.35 | 3.29 | 4.27 | 0.23 |
| AS/Sucrose-PB | 250 | 7.5 | 4 | 24 | 97 | 374 | 163.15 | 1.80 | 9.70 | 10.50 | 1.25 |
| AS/SPI | 350 | 6.5 | 4 | 24 | 100 | 548 | 151.55 | 1.01 | 13.76 | 14.49 | 1.89 |
| AS/SPI | 350 | 7.5 | 4 | 24 | 100 | 561 | 181.3 | 1.72 | 3.59 | 4.50 | 0.27 |
| AS/Sucrose PB | 350 | 7.5 | 4 | 24 | 101 | 376 | 157.69 | 1.11 | 12.00 | 12.81 | 1.62 |

SPI = sodium phosphate injection buffer (Marqibo kit component).
Sucrose PB = 10% sucrose in phosphate buffer (no NaCl)
AS = Ammonium Sulfate Example 3: Ammonium Sulfate VCR Liposome Encapsulation and Stability with Divalent Ions and Polyols A series of experiments were conducted to examine if VSLI containing divalent ions or polyols enhanced encapsulated vincristine.

Liposome variant preparations were made having the same lipid composition as Marqibo product, encapsulating 200 mM ammonium sulfate with either 200 mM magnesium sulfate or 200 mM manganese sulfate; 200 mM sodium citrate and either 200 mM magnesium sulfate or 200 mM manganese sulfate. Each of these preparations was diafiltered into 10% sucrose and the lipid concentration assayed as previously described. In addition, liposomes were prepared entrapping 250 mM ammonium sulfate with 5% mannitol-20 mM PB pH 7.4, SPI pH 7.4 and SPI pH 7.0 in the liposome. Drug loading was attempted for each variant incubating at either 10 minutes (standard condition) or 30 minutes 65° C. for 10 minutes.

reaffirmed the previously observed poor liposome loading efficiency in the presence of a divalent ion; 38% free drug was observed after constitution (Table 7). This mixed gradient variant was further processed by re-dialyzing to remove the external free vincristine. The post dialyzed variant was then monitored for stability. During 5 weeks of monitoring the free drug levels remained constant showing that no further leakage of the drug was occurring from the liposome. However a rapid degradation to NFV and loss of VCR was observed; resulting in 12.2% NFV at 5 weeks. This was 62 times more rapid than the 250 mM AS SPI pH 7.4 liposome formulation (FIG. 7). These results demonstrated that VSLI containing divalent sulfate does not provide improved stability of encapsulated vincristine.

The AS formulation with mannitol showed a degradation rate of 0.17% NFV/Month as compared to a non-polyol containing formulation at 0.14% NFV/Month (Table 7). However its encapsulation of only 93.4% vincristine was less efficient as those formulations without a polyol.

TABLE 7

Stability of VSLI for the Additional AS variants at 20 weeks.

| AS Variants | pH | Stability Temp ° C. | Stability Time, wks | % Free Drug | Total % Drug | % NFV | % NFV/ Mo |
|---|---|---|---|---|---|---|---|
| 200 mM AS/MgSO$_4$ | 7.4 | 4 | 5 | 38.1* | | 22.4 | 14.4 |
| 250 mM AS/ Mannitol-PB | 7.39 | 4 | 20 | 6.92 | 95.36 | 2.88 | 0.17 |
| 250 mM AS/SPI | 7.39 | 4 | 20 | 2.85 | 95.32 | 3.44 | 0.27 |
| 250 mM AS/SPI | 7.01 | 4 | 20 | 2.03 | 93.85 | 4.97 | 0.55 |

*After initial poor loading, variant was dialyzed to remove free VSI so T = 0 had 2.81% NF

EMBODIMENTS

Embodiment 1

A composition comprising: a continuous aqueous phase comprising a first aqueous buffer, a liposome phase dispersed within the first aqueous buffer, and a stabilizing aqueous solution encapsulated as cargo within the liposome phase; wherein the stabilizing aqueous solution comprises a second aqueous buffer and stabilized vincristine dissolved therein; wherein the second aqueous buffer comprises a salt having at least one solute that can transport out of the liposome phase and leave a positively charged solute or hydronium ion in the stabilizing aqueous solution, wherein the positively charged solute or hydronium ion stabilizes the vincristine; and wherein the continuous aqueous phase and the stabilizing aqueous solution have a pH difference of at least 2 pH units.

Embodiment 2

A method of stabilizing vincristine in a liposome comprising: dispersing a liposome phase within a continuous aqueous phase comprising a first aqueous buffer; wherein the liposome phase contains a stabilizing aqueous solution encapsulated as cargo within the liposome phase; wherein the stabilizing aqueous solution comprises a second aqueous buffer and stabilized vincristine dissolved therein; wherein the second aqueous buffer comprises a salt having at least one solute that can transport out of the liposome phase and leave a positively charged solute or hydronium ion in the stabilizing aqueous solution, wherein the positively charged solute or hydronium ion stabilizes the vincristine; and wherein the continuous aqueous phase and the stabilizing aqueous solution have a pH difference of at least 2 pH units.

Embodiment 3

The composition or method of embodiment 1 or 2, wherein the second aqueous buffer comprises an ammonium salt.

Embodiment 4

The composition or method of embodiment 1, 2, or 3, wherein the first aqueous buffer comprises a phosphate buffer solution.

Embodiment 5

The composition or method of embodiment 1, 2, 3, or 4, wherein the liposome phase comprises a sphingomyelin-cholesterol liposome.

Embodiment 6

The composition or method of embodiment 1, 2, 3, 4, or 5, wherein the second aqueous buffer comprises ammonium sulfate.

Embodiment 7

The composition or method of embodiment 1, 2, 3, 4, 5, or 6, wherein the vincristine comprises vincristine sulfate.

Embodiment 8

The composition or method of embodiment 1, 2, 3, 4, 5, 6, or 7, wherein the pH of the stabilizing aqueous solution is from about 3 to about 5.

Embodiment 9

The composition or method of embodiment 1, 2, 3, 4, 5, 6, 7, or 8, wherein the pH of the continuous aqueous phase is from about 5 to about 8.

Embodiment 10

The composition of embodiment 9, wherein the pH of the continuous aqueous phase is from about 7 to about 8.8.

Embodiment 11

The composition of embodiment 10, wherein the pH of the continuous aqueous phase is from about 7.5 to about 8.8.

Embodiment 12

The composition or method of embodiment 1, 2, 3, 4, 5, 6, 7, 8, 9, 10, or 11, wherein the liposome is hydrolysis resistant.

Embodiment 13

The composition or method of embodiment 1, 2, 3, 4, 5, 6, 7, 8, 9, 10, 11, or 12, wherein vincristine is more stable in the stabilizing aqueous solution than in the continuous aqueous phase.

Embodiment 14

The composition or method of embodiment 1, 2, 3, 4, 5, 6, 7, 8, 9, 10, 11, 12, or 13, wherein the ratio of the continuous aqueous phase and the stabilizing aqueous solution is such that mixing of the two phases would result in a combined aqueous phase with a pH from about 6 to about 8.8.

Embodiment 15

The composition or method of embodiment 1, 2, 3, 4, 5, 6, 7, 8, 9, 10, 11, 12, 13, or 14, wherein the ammonium salt is present in the second aqueous buffer at a concentration of about 150 mM to about 350 mM.

Embodiment 16

The composition or method of embodiment 1, 2, 3, 4, 5, 6, 7, 8, 9, 10, 11, 12, 13, 14, or 15, wherein the ammonium salt is ammonium sulfate.

Embodiment 17

A method of treating cancer in a mammal comprising administration of a therapeutic amount of the composition of embodiment 1, 3, 4, 5, 6, 7, 8, 9, 10, 11, 12, 13, 14, 15, or 16, to the mammal in need thereof.

Embodiment 18

The method of embodiment 17, wherein the cancer is lymphoma, leukemia, or myeloma.

Embodiment 19

A method of treating a relapse of cancer in a mammal comprising administering to said mammal the composition of embodiment 1, 3, 4, 5, 6, 7, 8, 9, 10, 11, 12, 13, 14, 15, or 16.

Embodiment 20

The method of embodiment 19, wherein the relapse of cancer is a lymphoma, leukemia, or myeloma.

Embodiment 21

The method of embodiment 17, 18, 19, or 20, wherein the mammal has previously undergone at least one multi-agent combination regime.

Embodiment 22

The method of embodiment 17, 18, 19, 20, or 21, further comprising co-administration of at least one other chemotherapeutic agent

Embodiment 23

The method of embodiment 17, 18, 19, 20, 21, or 22, wherein the mammal is a human.

Embodiment 24

A method of protecting vincristine against deformylation comprising mixing vincristine with an ammonium salt buffer.

Embodiment 25

The method of embodiment 23, wherein the vincristine is administered at a dose of from about 1.5 $mg/m^2$ to about 2.5 $mg/m^2$ Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. In one embodiment, the terms "about" and "approximately" refer to numerical parameters within 10% of the indicated range.

The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventor for carrying out the embodiments of the present disclosure. Of course, variations on these described embodiments will become apparent to those of ordinary skill in the art upon reading the foregoing description. The inventor expects skilled artisans to employ such variations as appropriate, and the inventor intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Furthermore, if any references have been made to patents and printed publications throughout this disclosure, each of these references and printed publications are individually incorporated herein by reference in their entirety.

In closing, it is to be understood that the embodiments disclosed herein are illustrative of the principles of the present disclosure. Other modifications that may be employed are within the scope of this disclosure. Thus, by way of example, but not of limitation, alternative configurations of the embodiments of the present disclosure may be utilized in accordance with the teachings herein. Accordingly, the present disclosure is not limited to that precisely as shown and described.

The invention claimed is:

1. A method of preventing vincristine degradation at room temperature for a period of 4 weeks comprising formulating the vincristine as the only active agent in a composition comprising;
    sphingomyelin-cholesterol liposomes consisting within them vincristine and an ammonium sulfate buffer at a pH of from about 3 to about 5, said liposomes dispersed within
    a continuous aqueous phase consisting of a phosphate buffer solution at a pH of from about 7 to about 8.8, and
    wherein the continuous aqueous phase and the ammonium sulfate buffer have a pH difference of at least 2 pH units.

2. The method of claim 1, wherein the vincristine comprises vincristine sulfate.

3. The method of claim 1, wherein the pH of the continuous aqueous phase is from about 7.1 to about 8.8.

4. The method of claim 1, wherein the vincristine is in a sulfate salt form.

5. The method of claim 1, wherein the liposome is hydrolysis resistant.

6. The method of claim 1, wherein the vincristine is more stable inside the liposome than in the continuous aqueous phase.

7. The method of claim 1, wherein the ratio of the continuous aqueous phase and the ammonium sulfate buffer is such that mixing of the two would result in a combined aqueous phase with a pH from about 6 to about 8.8.

8. The method of claim 1, wherein the ammonium sulfate is present at a concentration of about 150 mM to about 350 mM.

9. A method of treating cancer in a mammal comprising administration of a therapeutic amount of the composition of the method of claim 1 to the mammal in need thereof, wherein said cancer is lymphoma, leukemia, or myeloma.

10. The method of claim 9, wherein the cancer is lymphoma or myeloma.

11. The method of claim 9, wherein the vincristine is administered at a dose of from about 1.5 mg/m$^2$ to about 2.5 mg/m$^2$.

12. A method of treating a relapse of cancer in a mammal comprising administering to said mammal the composition of the method of claim 1, wherein said cancer is lymphoma, leukemia, or myeloma.

13. The method of claim 12, wherein the relapse of cancer is a lymphoma or myeloma.

14. The method of claim 12, wherein the mammal has previously undergone at least one multi-agent combination regime.

15. The method of claim 12, wherein said composition is co-administered with at least one additional chemotherapeutic agent.

16. The method of claim 12, wherein the mammal is a human.

17. A method of preventing vincristine degradation in a liposome for 4 weeks at room temperature comprising:
    dispersing sphingomyelin-cholesterol liposomes encapsulating vincristine and an ammonium sulfate buffer at a concentration of about 150 mM to about 350 mM within a continuous aqueous phase consisting of a phosphate buffer solution at a pH of about 6.5 to about 8.0;
    wherein the continuous aqueous phase and the ammonium sulfate buffer solution have a pH difference of at least 2 pH units.

18. The method of claim 17, wherein the vincristine comprises vincristine sulfate.

19. The method of claim 17, wherein the pH of the ammonium sulfate buffer is from about 3 to about 5.

20. The method of claim 17, wherein the vincristine is in a sulfate salt form.

21. The method of claim 17, wherein the liposome is hydrolysis resistant.

22. The method of claim 17, wherein the vincristine is more stable in the ammonium sulfate buffer than in the continuous aqueous phase.

23. The method of claim 17, wherein the ratio of the continuous aqueous phase and the ammonium sulfate buffer is such that mixing of the two would result in a combined aqueous phase with a pH from about 6 to about 8.8.

24. A method of preventing vincristine degradation for 12-24 months at 2° to 8° C. comprising formulating the vincristine in a composition comprising;
    sphingomyelin-cholesterol liposomes consisting within them vincristine and an ammonium sulfate buffer at a pH of from about 3 to about 5, said liposomes dispersed within
    a continuous aqueous phase consisting of a phosphate buffer solution at a pH of from about 7 to about 8.8,
    wherein the continuous aqueous phase and the ammonium sulfate buffer have a pH difference of at least 2 pH units.

25. A method of limiting vincristine degradation in a liposome for 12-24 months at 2° to 8° C. comprising:
    dispersing a liposome phase consisting of sphingomyelin-cholesterol liposomes encapsulating vincristine and an ammonium sulfate buffer at a concentration of about 150 mM to about 350 mM within a continuous aqueous phase consisting of a phosphate buffer solution at a pH of about 6.5 to about 8.0;
    wherein the continuous aqueous phase and the ammonium sulfate buffer have a pH difference of at least 2 pH units.

26. A vincristine composition formulated to limit vincristine degradation comprising;
    sphingomyelin-cholesterol liposomes consisting within them vincristine and an ammonium sulfate buffer at a pH of from about 3 to about 5, said liposomes dispersed within
    a continuous aqueous phase consisting of a phosphate buffer solution at a pH of from about 7 to about 8.8,
    wherein the continuous aqueous phase and the ammonium sulfate buffer have a pH difference of at least 2 pH units; and wherein the vincristine degradation rate is less than 1.5% N-desformylvincristine formation per month.

27. A method of reducing vincristine degradation in a liposome comprising:
dispersing a liposome phase consisting of sphingomyelin-cholesterol liposomes encapsulating vincristine and an ammonium sulfate buffer at a concentration of about 150 mM to about 350 mM within a continuous aqueous phase consisting of a phosphate buffer solution at a pH of about 6.5 to about 8.0;
wherein the continuous aqueous phase and the ammonium sulfate buffer have a pH difference of at least 2 pH units; and wherein the vincristine degradation rate is between about 0.1% and about 1.5% N-desformyl-vincristine formation per month.

28. A vincristine composition wherein vincristine is the only active agent, said composition comprising;
sphingomyelin-cholesterol liposomes consisting within them vincristine and an ammonium sulfate buffer at a pH of from about 3 to about 5, said liposomes dispersed within
a continuous aqueous phase consisting of a phosphate buffer solution at a pH of from about 7 to about 8.8,
wherein the continuous aqueous phase and the ammonium sulfate buffer have a pH difference of at least 2 pH units; and wherein the vincristine degradation rate is 1.5% N-desformylvincristine formation per month or less.

29. A method of reducing vincristine degradation in a liposome comprising:
dispersing a liposome phase consisting of sphingomyelin-cholesterol liposomes encapsulating vincristine and an ammonium sulfate buffer at a concentration of about 150 mM to about 350 mM within a continuous aqueous phase consisting of a phosphate buffer solution at a pH of about 6.5 to about 8.0;
wherein the continuous aqueous phase and the ammonium sulfate buffer have a pH difference of at least 2 pH units; and wherein the vincristine degradation rate is 1.5% N-desformylvincristine formation per month or less.

30. The composition of claim 26, wherein said NFV formation rate is 0.5% per month or less.

31. The method of claim 27, wherein said NFV formation rate is 0.5% per month or less.

32. The composition of claim 28, wherein said NFV formation rate is 0.5% per month or less.

33. The method of claim 29, wherein said NFV formation rate is 0.5% per month or less.

34. The method of claim 9, wherein said cancer comprises non-Hodgkin's Lymphoma.

35. A method of reducing vincristine degradation in a liposome wherein the vincristine is the sole active agent in the liposome, the method comprising:
dispersing sphingomyelin-cholesterol liposomes consisting within them vincristine and an ammonium sulfate buffer at a concentration of about 150 mM to about 350 mM within a continuous aqueous phase consisting of a phosphate buffer solution at a pH of about 8.1 to about 8.4;
wherein the continuous aqueous phase and the ammonium sulfate buffer have a pH difference of at least 2 pH units; and wherein the vincristine degradation rate is less than 1.5% N-desformylvincristine formation per month.

36. The composition of claim 28, wherein said pH is between 7.8 and 8.3.

37. The composition of claim 30, wherein said NFV formation rate is 0.2% per month or less.

38. The method of claim 31, wherein said NFV formation rate is 0.2% per month or less.

39. The composition of claim 32, wherein said NFV formation rate is 0.2% per month or less.

40. The method of claim 33, wherein said NFV formation rate is 0.2% per month or less.

* * * * *